United States Patent
Hermes et al.

(10) Patent No.: US 12,241,780 B2
(45) Date of Patent: Mar. 4, 2025

(54) SPECTROMETER DEVICE

(71) Applicant: trinamix GmbH, Ludwigshafen am Rhein (DE)

(72) Inventors: Wilfried Hermes, Ludwigshafen (DE); Sebastian Valouch, Ludwigshafen (DE); Robert Send, Karlsruhe (DE)

(73) Assignee: TRINAMIX GMBH, Ludwigshafen am Rhein (DE)

( * ) Notice: Subject to any disclaimer, the term of this patent is extended or adjusted under 35 U.S.C. 154(b) by 378 days.

(21) Appl. No.: 17/627,357

(22) PCT Filed: Jul. 16, 2020

(86) PCT No.: PCT/EP2020/070126
§ 371 (c)(1),
(2) Date: Jan. 14, 2022

(87) PCT Pub. No.: WO2021/009280
PCT Pub. Date: Jan. 21, 2021

(65) Prior Publication Data
US 2022/0268627 A1    Aug. 25, 2022

(30) Foreign Application Priority Data

Jul. 17, 2019 (EP) .................................... 19186717

(51) Int. Cl.
*G01J 3/02* (2006.01)
*G01J 3/28* (2006.01)
(Continued)

(52) U.S. Cl.
CPC .......... *G01J 3/0272* (2013.01); *G01J 3/0205* (2013.01); *G01J 3/0256* (2013.01); *G01J 3/2823* (2013.01);
(Continued)

(58) Field of Classification Search
None
See application file for complete search history.

(56) References Cited

U.S. PATENT DOCUMENTS

| | | | | |
|---|---|---|---|---|
| 5,784,507 A | * | 7/1998 | Holm-Kennedy ... | G02B 6/1228 385/36 |
| 6,608,677 B1 | * | 8/2003 | Ray ........................ | G01N 21/65 356/301 |

(Continued)

FOREIGN PATENT DOCUMENTS

| EP | 3156782 A1 | 4/2017 |
|---|---|---|
| JP | 2004354097 A | 12/2004 |

(Continued)

OTHER PUBLICATIONS

Wan et al ("Moving object detection based on high-speed video sequence images", 2019 IEEE 8th Joint ITAIC).*

(Continued)

*Primary Examiner* — Jonathan M Hansen
*Assistant Examiner* — Jarreas Underwood
(74) *Attorney, Agent, or Firm* — Armstrong Teasdale LLP

(57) ABSTRACT

Described herein is a spectrometer device. The spectrometer device is configured for determining at least one spectral or spectroscopic information of at least one object. The spectrometer device is configured for determining intensities of constituent wavelength signals of at least one light beam propagating from the object to the spectrometer device. The spectrometer device includes at least one distance detector configured for determining at least one distance information about a distance between at least one object and the spectrometer device, at least one pixelated imaging detector configured for determining at least one image of the object, and at least one evaluation device configured for determining at least one material information of the object by evaluating of at least one image of the object determined by (Continued)

the pixelated imaging detector. The evaluation device is configured for performing at least one spectroscopic analysis of the determined intensities of constituent wavelength signals.

18 Claims, 1 Drawing Sheet

(51) Int. Cl.
G01N 21/3504 (2014.01)
G01N 33/00 (2006.01)
G01N 33/02 (2006.01)
G06V 10/147 (2022.01)
G06V 10/60 (2022.01)
G06V 10/58 (2022.01)
G06V 20/68 (2022.01)

(52) U.S. Cl.
CPC ....... *G01N 21/3504* (2013.01); *G06V 10/147* (2022.01); *G06V 10/60* (2022.01); *G01N 33/0098* (2013.01); *G01N 33/02* (2013.01); *G06V 10/58* (2022.01); *G06V 20/68* (2022.01)

(56) References Cited

U.S. PATENT DOCUMENTS

| 2004/0130714 | A1 | 7/2004 | Gellerman et al. |
| 2006/0006337 | A1* | 1/2006 | Kane ................. G02B 26/0833 250/347 |
| 2006/0017914 | A1* | 1/2006 | Riess ................. G01N 21/3563 356/51 |
| 2008/0191137 | A1* | 8/2008 | Poteet ................. G01N 21/645 356/417 |
| 2009/0219524 | A1* | 9/2009 | Wang ................. G01J 3/28 356/301 |
| 2009/0219525 | A1* | 9/2009 | Marcus ................. G01J 3/02 356/301 |
| 2014/0291480 | A1 | 10/2014 | Bruder et al. |
| 2015/0010878 | A1* | 1/2015 | Seibel ................. A61B 5/0071 433/215 |
| 2015/0138538 | A1 | 5/2015 | Sakurai |
| 2016/0103073 | A1* | 4/2016 | Ford ................. G01J 3/0262 356/301 |
| 2017/0108450 | A1* | 4/2017 | von Chamier-Glisczinski ............ G06T 7/11 |
| 2018/0031468 | A1* | 2/2018 | Aphek ................. G01J 3/36 |
| 2018/0238735 | A1* | 8/2018 | Rosen ................. G01J 3/36 |
| 2019/0109431 | A1* | 4/2019 | Waterbury ............ G01J 3/0208 |

FOREIGN PATENT DOCUMENTS

| JP | 200591343 A | 4/2005 |
| WO | 2012110924 A1 | 8/2012 |
| WO | 2014097181 A1 | 6/2014 |
| WO | 2016120392 A1 | 8/2016 |
| WO | 2018019921 A1 | 2/2018 |
| WO | 2018091638 A1 | 5/2018 |
| WO | 2018091640 A2 | 5/2018 |
| WO | 2018091649 A1 | 5/2018 |
| WO | 2018167215 A1 | 9/2018 |
| WO | 2019042956 A1 | 3/2019 |

OTHER PUBLICATIONS

International Search Report and Written Opinion for corresponding PCT/EP2020/070126 mailed Dec. 23, 2020, 19 Pages.
Tom Funkhouser, "Image Processing COS 426, Spring 2014 Tom Funkhouser", Jan. 1, 2014.

* cited by examiner

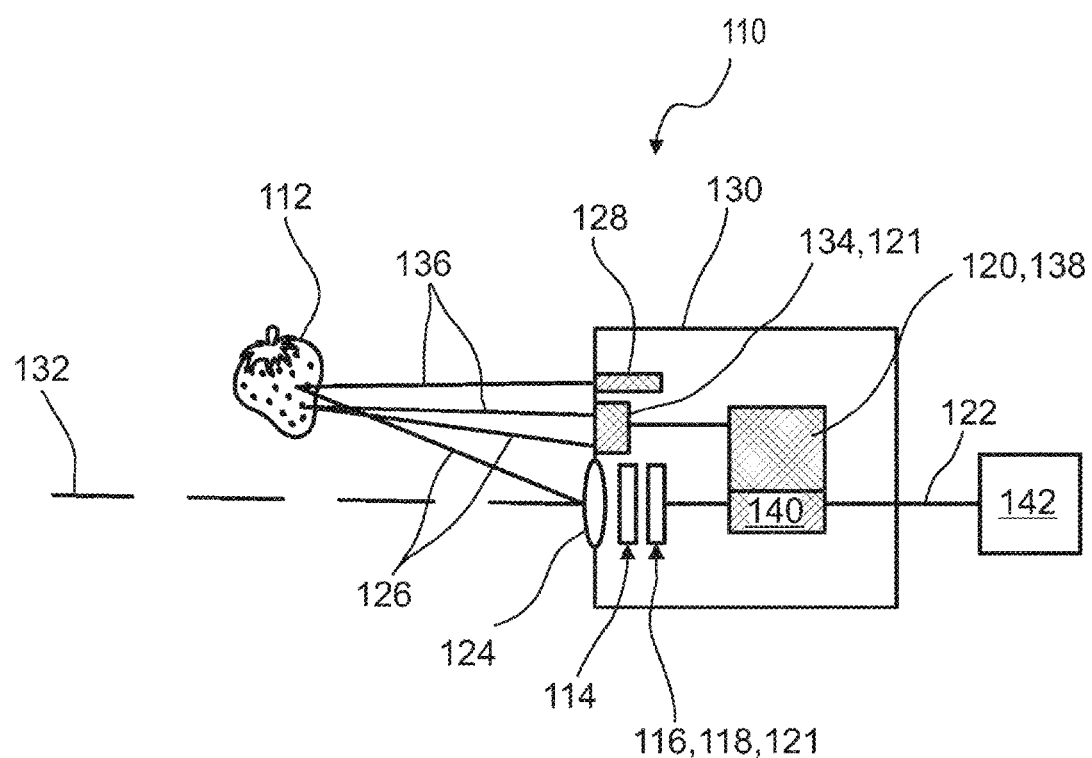

SPECTROMETER DEVICE

CROSS-REFERENCE TO RELATED APPLICATIONS

This application is a U.S. National Phase Application of International Patent Application No. PCT/EP2020/070126, filed Jul. 16, 2020, which claims priority to European Patent Application No. 19186717.5, filed Jul. 17, 2019, the entire contents of which are hereby incorporated by reference herein.

FIELD OF THE INVENTION

The invention relates to a spectrometer device, a method for determining at least one difference in at least one light property of at least one light beam originating from at least one object and to various uses of the spectrometer device. Such devices and methods can, in general, be employed for various applications for example, for investigation or monitoring purposes, in particular, an infrared detection application; a spectroscopy application; an exhaust gas monitoring application; a combustion process monitoring application; a pollution monitoring application; an industrial process monitoring application; a chemical process monitoring application; a food processing process monitoring application; a water quality monitoring application; an air quality monitoring application; a quality control application; a motion control application; an exhaust control application; a gas sensing application; a gas analytics application; a chemical sensing application; an agricultural application such as characterization of soil, silage, feed, crop or produce, monitoring plant health; a plastics identification and/or recycling application and the like. However, further kinds of applications are possible.

PRIOR ART

Various spectrometer devices and systems are known. A spectrometer generally emits light towards a sample or object and measures reflected, transmitted, scattered or received light. The spectroscopic analysis is based on the difference between the emitted and received light. The spectrometer determines wavelength dependent intensity differences before and after light interaction with the sample or object. The spectrometer may further determine properties such as wavelength dependent polarization differences.

To analyze differences in the light properties before and after interaction with the sample or object, it is important to measure these light properties with minimal alteration. In known spectrometers, pathway of interaction with the sample or object in spectrometers is therefore kept fixed and closed. However, there is a need for mobile spectrometers, wherein in mobile spectrometers, pathway of interaction may be variable, e.g. due to movement of the mobile spectrometer.

Spectrometer devices can work in a reflective or a transmissive mode, wherein in the reflect mode light is reflected from the sample and in the transmissive mode light is send through the sample. In case of opaque or nearly opaque samples, spectrometer devices working in the reflective mode may be advantageous. Further, for transmissive spectroscopy, often a cuvette or vial is filled with the sample. In reflective spectroscopy, it is possible to just touch the sample with the spectrometer or even measure it from a distance. Thus, reflective spectroscopy may be especially convenient in mobile spectroscopy.

However, in reflective spectroscopy, it is important to know the distance to the sample, as the light attenuation by the sample needs to be measured. In case of translucent or partially opaque samples, this distance becomes unclear or difficult to measure. Further, even in direct contact with the sample, it would be important to know the translucency parameters of the sample, to determine the attenuation according to the Beer-Lambert law.

Moreover, spectroscopy is used in consumer applications which include analysis of different samples for specific analytes. As an example, a consumer application may comprise determining lactose or fat content of a sample of milk. These consumer applications are often time consuming, difficult and non-reliable because of large variety of potential samples and analytes.

US 2008/191137 A1 describes a handheld Enhanced Photoemission Spectroscopy ("EPS") detection system which is utilized to identify specific substances (e.g., controlled substances, illegal drugs and explosives, and other substances of which trace detection would be of benefit) and mixtures thereof in order to provide information to officials for identification purposes and assists in determinations related to the legality, hazardous nature and/or disposition decision of such substance(s).

US 2009/219525 A1 describes a method that includes scanning a plurality of specimens with a laser by moving the laser according to coordinates for laser movement and measuring a distance for each of the plurality of specimens, associating location information with each of the specimens of the plurality of specimens based on its distance from the laser and its coordinates for laser movement, recording a Raman spectrum for the plurality of specimens, associating a Raman spectrum with each specimen of the plurality of specimens and indicating a Raman spectrum and location information for at least one specimen.

Problem Addressed by the Invention

It is therefore an object of the present invention to provide devices and methods facing the above-mentioned technical challenges of known devices and methods. Specifically, it is an object of the present invention to provide mobile spectroscopic devices and methods for mobile spectroscopy for contactless spectroscopy which reliably can determine spectroscopic information.

SUMMARY OF THE INVENTION

This problem is solved by the invention with the features of the independent patent claims. Advantageous developments of the invention, which can be realized individually or in combination, are presented in the dependent claims and/or in the following specification and detailed embodiments.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such a way with other optional or non-optional features of the invention.

In a first aspect of the present invention, a spectrometer device is disclosed. The term "spectrometer device" relates to an apparatus which is capable of recording signal intensity with respect to the corresponding wavelength of a spectrum or a partition thereof, such as a wavelength interval, wherein the signal intensity may, preferably, be provided as an electrical signal which may be used for further evaluation. The spectrometer device is configured for determining at least one spectral or spectroscopic information of at least one object. Specifically, the spectrometer device is configured for performing at least one spectroscopic measurement, also denoted spectroscopic analysis. As generally used, the term "spectrum" refers to a electromagnetic spectrum or wavelength spectrum. Specifically, the spectrum may be a partition of the visual spectral range and/or of the infrared (IR) spectral range, especially of the near-infrared (NIR) spectral range. Herein, each part of the spectrum is constituted by an optical signal which is defined by a signal wavelength and the corresponding signal intensity. The spectrometer device may be configured for transmission and/or reflection spectroscopy. For example, the spectrometer device may comprise at least one wavelength selective element, such as at least one linear variable filter element, at least one prism, at least one grating or the like, configured for separating incident light into a spectrum of constituent wavelength signals. The respective intensities of those wavelength signals may be determined by employing at least one pixelated optical detector and/or at least one grating and at least one single pixel detector, also denoted as single pixel optical detector, as will be outlined in more detail below. In case of using the at least one grating and the at least one single pixel detector a position of the grating may be changed gradually such that only one wavelength or a wavelength range having a narrow distribution may impinge on the single pixel detector. For example, the spectrometer device may be configured for absorption spectroscopy and may comprise, for example, at least one Fourier-transform infrared spectroscopy (FTIR) spectrophotometer. In this embodiment, the spectrometer device may comprise at least one broadband light source. The FTIR spectrophotometer may comprise at least one interferometer such as at least one Michelson interferometer. The FTIR spectrophotometer may be configured for illuminating the object with at least one light beam having time-dependent spectrum. The FTIR spectrophotometer may comprise at least one moving mirror element, wherein by movement of the mirror element a light beam generated by the broadband light source is alternatingly blocked and transmitted by the interferometer. The spectrometer device may furthermore comprise at least one Micro Electro Mechanical System (MEMS) configured for controlling the mirror element. The FTIR spectrophotometer may be configured for modulating the light beam depending on the wavelength such that different wavelengths are modulated at different rates. The FTIR spectrophotometer may comprise at least one fixed detector configured for detect an absorption spectrum of the light beam having passed the object. For example, the FTIR spectrophotometer may comprise at least one single pixel optical detector.

As used herein, the term "light", generally, refers to a partition of electromagnetic radiation which is, usually, referred to as "optical spectral range" and which comprises one or more of the visible spectral range, the ultraviolet spectral range and the infrared spectral range. Herein, the term "ultraviolet spectral range", generally, refers to electromagnetic radiation having a wavelength of 1 nm to 380 nm, preferably of 100 nm to 380 nm. Further, in partial accordance with standard ISO-21348 in a valid version at the date of this document, the term "visible spectral range", generally, refers to a spectral range of 380 nm to 760 nm. The term "infrared spectral range" (IR) generally refers to electromagnetic radiation of 760 nm to 1000 µm, wherein the range of 760 nm to 1.5 µm is usually denominated as "near infrared spectral range" (NIR) while the range from 1.5µ to 15 µm is denoted as "mid infrared spectral range" (MidIR) and the range from 15 µm to 1000 µm as "far infrared spectral range" (FIR). Preferably, light used for the typical purposes of the present invention is light in the infrared (IR) spectral range, more preferred, in the near infrared (NIR) and the mid infrared spectral range (MidIR), especially the light having a wavelength of 1 µm to 5 µm, preferably of 1 µm to 3 µm.

The spectrometer device is configured for determining intensities of constituent wavelength signals of at least one light beam propagating from the object to the spectrometer device. The spectrometer device comprises at least one distance detector. The distance detector is configured for determining at least one distance information about a distance between the at least one object and the spectrometer device. The spectrometer device comprises at least one pixelated imaging detector configured for determining at least one image of the object. The spectrometer device comprises at least one evaluation device. The evaluation device is configured for determining at least one material information of the object by evaluating of at least one image of the object determined by the pixelated imaging detector. The evaluation device is configured for performing at least one spectroscopic analysis of the determined intensities of constituent wavelength signals considering the determined distance information and the material information.

The spectrometer device is configured for determining intensities of constituent wavelength signals of at least one light beam propagating from the object to the spectrometer device. For example, the spectrometer device may comprise at least one wavelength selective element, such at least one linear variable filter element, at least one prism, at least one grating or the like, configured for separating incident light into a spectrum of constituent wavelength signals. The respective intensities of those wavelength signals may be determined by employing at least one pixelated optical detector and/or at least one grating and at least one single pixel detector. As used herein, the term "wavelength selective element" refers to an optical element which is adapted for separating incident light into the spectrum of constituent wavelength signals. For example, the wavelength selective element may be or may comprise at least one linear variable filter element, at least one prism, at least one grating or the like. For example, the wavelength selective element may be and/or may comprise at least one optical filter such as a length variable filter, i.e. an optical filter which comprises a plurality of filters, preferably a plurality of interference filters, which may, in particular, be provided in a continuous arrangement of the filters. Herein, each of the filters may form a bandpass with a variable center wavelength for each spatial position on the filter, preferably continuously, along a single dimension, which is, usually, denoted by the term "length", on a receiving surface of the length variable filter. In a preferred example, the variable center wavelength may be a linear function of the spatial position on the filter, in which case the length variable filter is usually referred to as a "linearly variable filter" or by its abbreviation "LVF". However, other kinds of functions may be applicable to the relationship between the variable center wavelength and the spatial position on the filter. Herein, the filters may be located on a transparent substrate which may, in particular, comprise at least one material that may show a high degree of optical transparency within in the visual and/or infrared (IR) spectral range, especially, within the near-infrared (NIR) spectral range as described below in more detail, whereby varying spectral properties, especially continuously varying spectral properties, of the filter along length of the filter may be achieved. In particular, the wavelength selective element may be a wedge filter that may be adapted to carry at least one response coating on a transparent substrate, wherein the response coating may exhibit a spatially variable property, in particular, a spatially variable thickness. However, other kinds of length variable filters which may comprise other materials or which may exhibit a further spatially variable property may also be feasible. At a normal angle of incidence of an incident light beam, each of the filters as comprised by the length variable filter may have a bandpass width that may amount to a fraction of the center wavelength, typically to a few percent, of the particular filter. By way of example, for a length variable filter having a wavelength range from 1400 to 1700 nm and a bandpass width of 1%, the bandpass width at the normal incidence angle might vary from 14 nm to 17 nm. However, other examples may also be feasible. As a result of this particular set-up of the length variable filter, only incident light having a wavelength which may, within a tolerance indicated by the bandpass width, equal the center wavelength being assigned to a particular spatial position on the filter is able to pass through the length variable filter at the particular spatial position. Thus, a "transmitting wavelength" which may be equal to the center wavelength±½ of the bandpass width may be defined for each spatial position on the length variable filter. In other words, all light which may not pass through the length variable filter at the transmitting wavelength may be absorbed or, mostly, reflected by the receiving surface of the length variable filter. As a result, the length variable filter has a varying transmittance which may enable it for separating the incident light into a spectrum.

The spectrometer device may comprise at least one spectrum detector configured for determining intensities of constituent wavelength signals of at least one light beam propagating from the object to the spectrometer device. The spectrum detector may comprise at least one pixelated optical detector configured for determining intensities of constituent wavelength signals. The spectrum detector may comprise a matrix of optical sensors. The optical sensors of the spectrum detector each may have a light-sensitive area. Each optical sensor of the spectrum detector may be configured to generate at least one sensor signal in response to an illumination of the light-sensitive area by at least one light beam propagating from at least one object to the spectrometer device. The spectrum detector may comprise a series of optical sensors which may, preferably, be arranged in a single line as a one-dimensional matrix along the length of the length variable filter or in more than one line, especially as two, three, or four lines parallel lines, in form of a two-dimensional matrix, in particular, in order to receive most of the intensity of the incident light as possible. Thus, a number N of pixels in one direction may be higher compared to a number M of pixels in a further direction such that the one-dimensional 1×N matrix or a rectangular two-dimensional M×N matrix may be obtained, wherein M<10 and N≥10, preferably N≥20, more preferred N≥50. In addition, the matrixes used herein may also be placed in a staggered arrangement. Herein, each of the optical sensors of the spectrum detector as used therein may have the same or, within a tolerance level, a similar optical sensitivity, especially for ease of manufacturing the series of the optical sensors. However, other kinds of arrangements may also be feasible. For example, as outlined above, the spectrometer device may be configured for absorption spectroscopy and may comprise, for example, at least one Fourier-transform infrared spectroscopy (FTIR) spectrophotometer. In particular, the FTIR spectrophotometer may comprise at least one single pixel optical detector.

Each of the optical sensors of the spectrum detector may be adapted to receive at least a portion of one of the constituent wavelength signals. Each of the constituent wavelength signals is related to an intensity of each constituent wavelength. The light which may pass through the wavelength selective element at a particular spatial position on the wavelength selective element may, subsequently, impinge on the spectrum detector. In other words, the spectrum detector may, preferably, be placed in a manner that the light may first impinge on the wavelength selective element and only that the partition of the light which may pass through the particular spatial position on the wavelength selective element may, thereafter, be capable of impinging on a corresponding spatial position on the pixelated optical detector of the spectrum detector.

As a result, the wavelength selective filter element may, therefore, be used for separating the incident light by its associated wavelength or wavelengths into at least one corresponding spatial position while a particular optical sensor comprised by the pixelated optical detector may, consequently, be employed for measuring an intensity of the incident light which, due to its particular wavelength, may be able to pass through the wavelength selective filter element at the corresponding spatial position and, therefore, impinge the particular optical sensors provided for determining the intensity of the incident light at the particular wavelength. In a particularly preferred embodiment, the detector may, thus, comprise a sequence of optical sensor which may be located in form of a series of optical sensors one following the other, wherein the sequence of the optical sensors of the spectrum detector may be placed in a parallel manner with respect to the continuous arrangement of the interference filters along the length of the wavelength selective element.

In particular, in order to achieve a high resolution of the spectrometer device, each of the optical sensors of the spectrum detector may, thus, be adapted to receive incident light only over a small spatial angle. This arrangement, particularly, reflects the setup of the wavelength selective element which is designed to generate the desired spectrum depending on the spatial position of the impingement of the incident light along the length of the wavelength selective element. This particular arrangement may be achieved by a spectrum detector which comprises a plurality of pixelated optical detectors, wherein each of the pixelated optical detectors is adapted to receive at least a portion of one of the constituent wavelength signals as provided by the length variable filter. As indicated above, each of the constituent wavelength signals is, hereby, related to an intensity of each of the constituent wavelengths. As generally used, the terms "pixelated optical detector" or "pixelated optical sensor" refers to an optical detector which comprises an array of individual pixel sensors, wherein each of the individual pixel sensors has at least a photosensitive area which is adapted for generating an electrical signal depending on the intensity of the incident light, wherein the electrical signal may, in particular, be provided to the evaluation device for further evaluation. Herein, the photosensitive area as comprised by each of the individual optical sensors may, especially, be a single, uniform photosensitive area which is configured for receiving the incident light which impinges on the individual optical sensor. However, other arrangements of the optical sensors may also be conceivable.

The spectrum detector may be designed to generate signals, preferably electronic signals, associated with the intensity of the incident light which impinges on the individual optical sensor. The signal may be an analogue and/or a digital signal. The electronic signals for adjacent optical sensors can, accordingly, be generated simultaneously or else in a temporally successive manner. By way of example, during a row scan or line scan, it is possible to generate a sequence of electronic signals which correspond to the series of the individual pixels which are arranged in a line. In addition, the individual optical sensors may, preferably, be active pixel sensors which may be adapted to amplify the electronic signals prior to providing it to the external evaluation unit. For this purpose, the spectrum detector may comprise one or more signal processing devices, such as one or more filters and/or analogue-digital-converters for processing and/or preprocessing the electronic signals.

The spectrum detector may be selected from any known pixel sensor, in particular, from a pixelated organic camera element, preferably, a pixelated organic camera chip, or from a pixelated inorganic camera element, preferably, a pixelated inorganic camera chip, more preferably from a CCD chip or a CMOS chip, which are, commonly, used in various cameras nowadays. As an alternative, the spectrum detector may be or comprise a photoconductor or photodiode based on materials such as PbS, PbSe, Ge, InGaAs, ext. InGaAs, InSb, or HgCdTe. As a further alternative it may comprise of pyroelectric, bolometer or thermopile detector elements. Thus, a camera chip having a matrix of 1×N pixels or of M×N pixels may be used here, wherein $M<10$ and $N \geq 10$, preferably $N \geq 20$, more preferred $N \geq 50$. Further, a mono-chrome camera element, preferably a monochrome camera chip, may be used, wherein the monochrome camera element may be differently selected for each pixel sensor, especially, in accordance with the varying wavelength along the series of the optical sensors.

The spectrum detector may be adapted to provide a plurality of the electrical signals which may be generated by the photosensitive areas of the optical sensors comprised by the pixelated optical detector. The electrical signals as provided by the pixelated optical detector of the spectrometer device may, subsequently, be forwarded to the evaluation device. Herein, the term "evaluation device" refers to an apparatus being designated for determining information related to the spectrum of the object of which a spectrum has been recorded, in particular, by using the spectrometer device as described herein, wherein the information is obtainable by evaluating the detector signals as provided by the detector of the spectrometer device. The information may, for example, be provided electronically, visually, acoustically or in any arbitrary combination thereof. Further, the information may be stored in a data storage device of the spectrometer device or of a separate storage device and/or may be provided via at least one interface, such as a wireless interface and/or a wire-bound interface.

The spectrometer device may comprise at least one concentrator device, also denoted light concentrator, for directing the light beam to the wavelength selective element. As generally used, the term "concentrator device" refers to a non-imaging optical element having an input, also denoted as "entrance pupil" or "entrance aperture, an output located oppositely to the input, wherein the output may also be denoted by one of the terms "exit pupil" or "exit aperture", and an optically guiding structure located between the input and the output, wherein the concentrator device is, in normal direction of operation, adapted for capturing light at the input at a large angular spread, concentrating the captured light within the optically guiding structure, and emitting the concentrated light at the output. In the spectrometer device, the concentrator device may be used in a reversed operation mode, wherein the entrance pupil facing towards the object may be the smaller aperture of concentrator device, in order to capture only the light from the object, wherein the exit pupil facing the spectrum detector may be the larger aperture of the concentrator device in order to distribute all of the collected light onto the pixelated optical detector. By way of example, the optical concentrator may, therefore, be used in concentrated photovoltaics in order to allow high solar concentration under large possible entrance angles. For example, the concentrator device may be selected from the group selected of: at least one tapered or conic light concentrator, a compound parabolic concentrator, a compound elliptical concentrator, and a compound hyperbolic concentrator.

In addition, the spectrometer device may further comprise at least one transfer device. The light beam which emerges from the object may travel firstly through the transfer device until it may, subsequently, pass the wavelength selective element until it may, finally, impinge the spectrum detector. As used herein, the term "transfer device" may, thus, refer to an optical component which can be configured to transfer the light beam emerging from the inversely-operated optical concentrator device to the spectrum detector. In a particular embodiment, the transfer device can, thus, be designed to shape the light beam before it may be guided to the length variable filter. Particularly, the transfer device may be selected from a group consisting of an optical lens, a mirror, a grating, and a diffractive optical element. More particular, the optical lens may, especially, be selected from a group consisting of a biconvex lens, a plano-convex lens, a biconcave lens, a plano-concave lens, an aspherical lens, a cylindrical lens and a meniscus lens. Hereby, the transfer device may comprise a material which may be at least partially transparent, preferably over the whole wavelength range of the wavelength selective element as indicated above. For this purpose, the same or similar optically transparent materials as mentioned in this respect can also be used. However, further optical elements may also be feasible.

Light emerging from the object can originate in the object itself, but can also optionally have a different origin and propagate from this origin to the object and subsequently toward the spectrometer device. The latter case can, in particular, be affected by at least one illumination source being used. Thus, the light propagating from the object to the spectrometer device may be light which may be reflected and/or scattered by the object. Alternatively or in addition, the light may at least partially transmitted through the object.

The spectrometer device may comprise at least one illumination source. As used herein, the term "illumination source" refers to an arbitrary device adapted to generate and/or to provide at least one light beam for illumination of the object. The illumination source can be embodied in various ways. Thus, the illumination source can be for example part of the spectrometer device in a housing. Alternatively or additionally, however, the at least one illumination source can also be arranged outside a housing, for example as a separate light source. The illumination source can be arranged separately from the object and illuminate the object from a distance. As indicated above, the illumination source can, alternatively or in addition, also be connected to the object or be part of the object, such that, by way of example, the electromagnetic radiation emerging from the object can also be generated directly by the illumination source. By way of example, at least one illumination source can be arranged on and/or in the object and directly generate the electromagnetic radiation.

The illumination source may, preferably, comprise a kind of light emitting element such as a thermal radiation source which may be known to provide sufficient emission in visual spectral range and/or in the infrared (IR) spectral range, especially, in the near infrared (NIR) spectral range, in particular, an incandescent lamp and/or thermal infrared emitters, e.g. micro-machined thermal infrared emitters available under emirs50 from Axetris AG, Schwarzenbergstrasse 10, CH-6056 Kagiswil, Switzerland, thermal infrared emitters from LASER COMPONENTS GmbH, Werner-von-Siemens-Str. 15 82140 Olching, Germany, or infrared emitters from Hawkeye Technologies, 181 Research Drive #8, Milford CT 06460, United States. Alternatively or in addition, the illumination source may, be selected from at least one of the following illumination sources: a laser, in particular a laser diode, although further types of lasers can also be used; a light emitting diode; an organic light source, in particular an organic light emitting diode; a neon light; a structured light source; a flame source; a heat source. Alternatively or additionally, other illumination sources can be used. Herein, it may particularly be preferred when the light emitted by the object and/or by the illumination source may exhibit a spectral range which may be closely related to the spectral sensitivities of the detector, particularly, in a manner to ensure that the detector which may be illuminated by the respective illumination source may be capable of providing a detector signal having a high intensity, thus, enabling an evaluation of the detector signals with sufficient signal-to-noise-ratio and, concurrently, a high-resolution. The spectrum detector may be sensitive in the range of the emission of the illumination source.

The spectrometer device comprises at least one distance detector. As used herein, the term "distance detector" may refer to an arbitrary device configured for determining distance information about a distance between the object and the spectrometer device, in particular at least one longitudinal coordinate of the object. The distance detector may comprise at least one pixelated optical detector. The pixelated optical detector of the distance detector may be a designed as further pixelated optical detector and/or the spectrum detector, as described above or in more detail below, may be used as pixelated optical detector of the distance detector. For example, the spectrum detector and the pixelated optical detector of the distance detector may be designed identical or different. The spectrometer device may be configured for determining the distance information and the information related to the spectrum of the object simultaneously or subsequently.

The spectrometer device may constitute a coordinate system, wherein a longitudinal coordinate is a coordinate along an optical axis of the spectrometer device. The coordinate system may be a polar coordinate system in which the optical axis of the spectrometer device forms a z-axis and in which a distance from the z-axis and a polar angle may be used as additional coordinates. A direction parallel or anti-parallel to the z-axis may be considered a longitudinal direction, and a coordinate along the z-axis may be considered a longitudinal coordinate or distance. Any direction perpendicular to the z-axis may be considered a transversal direction, and the polar coordinate and/or the polar angle may be considered a transversal coordinate. As used herein, the term "distance information" refers to information about the longitudinal coordinate of the object and/or a distance value between spectrometer device and the object. As used herein, the term "determining at least one distance information" refers to obtaining and/or measuring and/or deriving and/or estimating the distance information. The distance between the object and the spectrometer device may be obtained by using one or more of the following techniques: depth-from-photon-ratio, structured light, beam profile analysis, time-of-flight, shape-from-motion, depth-from-focus, triangulation, depth-from-defocus, stereo sensors. Furthermore, the distance information may be obtained using at least one FiP sensor as described in WO 2012/110924 A1 or WO 2014/097181 A1. Additionally or alternatively, the distance detector may be configured for determining the distance between the object and the spectrometer device based on triangulation principle, such as at least one triangulation proximity sensor. The distance detector may comprise at least one time-of-flight sensor. For example, at least one of the optical sensors may be adapted to generate at least one sensor signal dependent on a time-of-flight (TOF) the illumination light beam has traveled from the illumination source to the object and a reflection light beam has traveled from the object to the time-of-flight sensor. The time-of-flight sensor may be selected from the group consisting of: at least one pulsed time-of-flight detector; at least one phase modulated time-of-flight detector; at least one direct time-of-flight detector; at least one indirect time-of-flight detector. For example, the pulsed time-of-flight detector may be at least one range gated imager and/or at least one direct time-of-flight imager. For example the phase modulated time-of-flight detector may be at least one RF-modulated light source with at least one phase detector. The time-of-flight sensor may be adapted to determine a time delay between emission of the illumination light beam by the illumination source and receipt of the reflection light beam.

The spectrometer device may be adapted to perform the determination of the distance information, such as the longitudinal coordinate, before and/or during and/or after the spectroscopic measurement.

Preferably, the spectrometer device, in particular the distance detector, may be adapted to determine the position based on the depth-from-photon-ratio technique. With respect to details of methods and devices based on the depth-from-photon-ratio technique reference is made to international patent applications number PCT/EP2017/079577, PCT/EP2017/079558, PCT/EP2017/079564 filed on Nov. 17, 2017 and PCT/EP2018/056545 filed on Mar. 15, 2018 the full content of which is included by reference. Depth-from-photon-ratio is a distance measurement technology that is very flexible concerning the detector technology and, thus, also very flexible concerning the wavelength of the employed light source. Known mobile spectrometer technologies use silicon, InAs, InGaAs, or extended InGaAs detectors, wherein silicon is very limited in its wavelength regime and both InAs and InGaAs are expensive. Lead salt detectors show promise for mobile applications due to novel encapsulation technologies allowing compact sensor designs, see e.g. WO 2018/019921 A1. Using depth-from-photon-ratio may allow reliable distance measurement and easy implementation in a spectrometer with little additional effort.

The pixelated optical detector of the distance detector may comprise the at least one sensor element having a matrix of optical sensors. For example, the spectrum detector, as described above or in more detail below, may be used as pixelated optical detector of the distance detector. Additionally or alternatively, the spectrometer device may comprise in addition to the spectrum detector a sensor element having a matrix of optical sensors. The optical sensors of the distance detector each may have a light-sensitive area. Each optical sensor of the distance detector may be configured for generating at least one sensor signal, denoted in the following as "distance" sensor signal", in response to an illumination of the light-sensitive area by at least one light beam propagating from at least one object to the spectrometer device. At least one first optical sensor of the optical sensors of the distance detector may be adapted to generate a first sensor signal in response to illumination by a first constituent wavelength and at least one second optical sensor of the optical sensors of the distance detector may be adapted to generate a second sensor signal in response to an illumination by the first constituent wavelength. The evaluation device may be configured for determining at least one longitudinal coordinate z of the object by evaluating a combined signal Q from the first sensor signal and the second sensor signal. The evaluation device may be configured for evaluating at least one sensor signal generated by the spectrum detector by performing at least one spectroscopic analysis considering the determined longitudinal coordinate z.

As used herein, an "optical sensor" generally refers to a light-sensitive device for detecting a light beam, such as for detecting an illumination and/or a light spot generated by at least one light beam. As further used herein, a "light-sensitive area" generally refers to an area of the optical sensor which may be illuminated externally, by the at least one light beam, in response to which illumination at least one sensor signal is generated. The light-sensitive area may specifically be located on a surface of the respective optical sensor. Other embodiments, however, are feasible. The spectrometer device may comprise a plurality of optical sensors each having a light sensitive area. As used herein, the term "the optical sensors each having at least one light sensitive area" refers to configurations with a plurality of single optical sensors each having one light sensitive area and to configurations with one combined optical sensor having a plurality of light sensitive areas. The term "optical sensor" furthermore refers to a light-sensitive device configured to generate one output signal.

Each optical sensor of the distance detector may be embodied such that precisely one light-sensitive area is present in the respective optical sensor, such as by providing precisely one light-sensitive area which may be illuminated, in response to which illumination precisely one uniform sensor signal is created for the whole optical sensor. Thus, each optical sensor of the distance detector may be a single area optical sensor. The use of the single area optical sensors, however, renders the setup of the detector specifically simple and efficient. Thus, as an example, commercially available photo-sensors, such as commercially available silicon photodiodes, each having precisely one sensitive area, may be used in the set-up. Other embodiments, however, are feasible. The optical sensors of the distance detector may be part of or constitute a pixelated optical device. For example, the optical sensor of the distance detector may be and/or may comprise at least one CCD and/or CMOS device. As an example, the optical sensors of the distance detector may be part of or constitute at least one CCD and/or CMOS device having a matrix of pixels, each pixel forming a light-sensitive area.

The optical sensors for determining the distance information and the optical sensors used for spectroscopy may be identical. Specifically, the optical sensors for determining the distance information may be used as optical sensors for spectroscopy or the other way round. Thus, the optical sensors for determining the distance information may correspond to or may be designed as the optical sensors for spectroscopy and/or the matrix of optical sensors of the sensor element may correspond to or may be designed as pixelated optical detector.

The optical sensors of the distance detector specifically may be or may comprise at least one photodetector, preferably inorganic photodetectors, more preferably inorganic semiconductor photodetectors, most preferably silicon photodetectors. Specifically, the optical sensors of the distance detector may be sensitive in the infrared spectral range. All pixels of the matrix or at least a group of the optical sensors of the matrix specifically may be identical. Groups of identical pixels of the matrix specifically may be provided for different spectral ranges, or all pixels may be identical in terms of spectral sensitivity. Further, the pixels may be identical in size and/or with regard to their electronic or optoelectronic properties. Specifically, the optical sensors may be or may comprise at least one inorganic photodiode which are sensitive in the infrared spectral range, preferably in the range of 700 nm to 3.0 micrometers. Specifically, the optical sensors may be sensitive in the part of the near infrared region where silicon photodiodes are applicable specifically in the range of 700 nm to 1100 nm. Infrared optical sensors which may be used for optical sensors may be commercially available infrared optical sensors, such as infrared optical sensors commercially available under the brand name Hertzstueck™ from trinamiX GmbH, D-67056 Ludwigshafen am Rhein, Germany. Thus, as an example, the optical sensors may comprise at least one optical sensor of an intrinsic photovoltaic type, more preferably at least one semiconductor photodiode selected from the group consisting of: a Ge photodiode, an InGaAs photodiode, an extended InGaAs photodiode, an InAs photodiode, an InSb photodiode, a HgCdTe photodiode. Additionally or alternatively, the optical sensors may comprise at least one optical sensor of an extrinsic photovoltaic type, more preferably at least one semiconductor photodiode selected from the group consisting of: a Ge:Au photodiode, a Ge:Hg photodiode, a Ge:Cu photodiode, a Ge:Zn photodiode, a Si:Ga photodiode, a Si:As photodiode.

Additionally or alternatively, the optical sensors may comprise at least one photoconductive sensor such as a PbS or PbSe sensor, a bolometer, preferably a bolometer selected from the group consisting of a VO bolometer and an amorphous Si bolometer.

The matrix of the distance detector may be composed of independent pixels such as of independent optical sensors. Thus, a matrix of inorganic photodiodes may be composed. Alternatively, however, a commercially available matrix may be used, such as one or more of a CCD detector, such as a CCD detector chip, and/or a CMOS detector, such as a CMOS detector chip. Thus, generally, the optical sensor of the distance detector may be and/or may comprise at least one CCD and/or CMOS device and/or the optical sensors of the detector may form a sensor array or may be part of a sensor array, such as the above-mentioned matrix. Thus, as an example, the optical sensors of the distance detector may comprise and/or constitute an array of pixels, such as a rectangular array, having m rows and n columns, with m, n, independently, being positive integers. For example, the sensor element of the distance sensor may comprise a line sensor, wherein n or m are equal to 1. For example, the sensor element of the distance detector may comprise at least two optical sensors arranged in a row and or column such as a bi-cell. For example, the sensor element of the distance detector may a quadrant diode system comprising a 2×2 matrix of optical sensors. For example, more than one column and more than one row is given, i.e. n>1, m>1. Thus, as an example, n may be 2 to 16 or higher and m may be 2 to 16 or higher. Preferably, the ratio of the number of rows and the number of columns is close to 1. As an example, n and m may be selected such that $0.3 \leq m/n \leq 3$, such as by choosing m/n=1:1, 4:3, 16:9 or similar. As an example, the array may be a square array, having an equal number of rows and columns, such as by choosing m=2, n=2 or m=3, n=3 or the like.

The matrix of the distance detector specifically may be a rectangular matrix having at least one row, preferably a plurality of rows, and a plurality of columns. As an example, the rows and columns may be oriented essentially perpendicular. As used herein, the term "essentially perpendicular" refers to the condition of a perpendicular orientation, with a tolerance of e.g. ±20° or less, preferably a tolerance of ±10° or less, more preferably a tolerance of ±5° or less. Similarly, the term "essentially parallel" refers to the condition of a parallel orientation, with a tolerance of e.g. ±20° or less, preferably a tolerance of ±10° or less, more preferably a tolerance of ±5° or less. Thus, as an example, tolerances of less than 20°, specifically less than 10° or even less than 5°, may be acceptable. In order to provide a wide range of view, the matrix specifically may have at least 10 rows, preferably at least 500 rows, more preferably at least 1000 rows. Similarly, the matrix may have at least 10 columns, preferably at least 500 columns, more preferably at least 1000 columns. The matrix may comprise at least 50 optical sensors, preferably at least 100000 optical sensors, more preferably at least 5000000 optical sensors. The matrix may comprise a number of pixels in a multi-mega pixel range. Other embodiments, however, are feasible. Thus, in setups in which an axial rotational symmetry is to be expected, circular arrangements or concentric arrangements of the optical sensors of the matrix, which may also be referred to as pixels, may be preferred.

Preferably, the light sensitive areas of the optical sensors of the distance detector may be oriented essentially perpendicular to an optical axis of the spectrometer device. The optical axis may be a straight optical axis or may be bent or even split, such as by using one or more deflection elements and/or by using one or more beam splitters, wherein the essentially perpendicular orientation, in the latter cases, may refer to the local optical axis in the respective branch or beam path of the optical setup.

For determining a longitudinal coordinate of the object using depth-from-photon-ratio technology at least two optical sensors of the distance detector may be employed. As outlined above, for obtaining the distance information the spectrometer device comprises at least one optical sensor and/or a plurality of optical sensors. Specifically, for spectroscopy, one optical sensor in combination with a prism or several optical sensors in combination with an optical filer may be employed. For example, one of the optical sensors used for determining a longitudinal coordinate of the object using depth-from-photon-ratio technology may be employed for spectroscopy. For example, the pixelated optical detector may be configured for spectroscopy and for determining the longitudinal coordinate of the object using depth-from-photon-ratio technology. Thus, using depth-from-photon-ratio may allow reliable distance measurement and easy implementation in a spectrometer with little additional effort.

As used herein, a "sensor signal" generally refers to a signal generated by the optical sensor and/or at least one pixel of the optical sensor in response to illumination. Specifically, the sensor signal may be or may comprise at least one electrical signal, such as at least one analogue electrical signal and/or at least one digital electrical signal. More specifically, the sensor signal may be or may comprise at least one voltage signal and/or at least one current signal. More specifically, the sensor signal may comprise at least one photocurrent. Further, either raw sensor signals may be used, or the pixelated optical detector of the distance detector, the optical sensor of the distance detector or any other element may be adapted to process or preprocess the sensor signal, thereby generating secondary sensor signals, which may also be used as sensor signals, such as preprocessing by filtering or the like. The terms "first" and "second" sensor signal and constituent wavelength are used as names and give no indication of an order or whether further sensor signals and constituent wavelength are used. Each optical sensor of the matrix of optical sensors may be configured to generate at least one sensor signal in response to an illumination of the light-sensitive area by at least one light beam, in particular having one constituent wavelength, propagating from at least one object to the spectrometer device. At least one first optical sensor of the optical sensors of the distance detector may be adapted to generate a first sensor signal in response to illumination by a first constituent wavelength and at least one second optical sensor of the optical sensors of the distance detector may be adapted to generate a second sensor signal in response to an illumination by the first constituent wavelength.

As outlined above, the evaluation device may be adapted to evaluate the combined signal. Thereby, the at least one longitudinal coordinate of the object is determined. As used herein, the term "longitudinal coordinate of the object" refers to a distance between the matrix of optical sensors of the distance detector and the object. The evaluating may comprises evaluating the combined signal from the first sensor signal and the second sensor signal. As used herein, the term "combined signal" refers to a signal which is generated by combining at least two sensor signals, in particular by one or more of dividing the sensor signals, dividing multiples of the sensor signals or dividing linear combinations of the sensor signals. The evaluation device may be configured for deriving the combined signal by one or more of dividing the sensor signals, dividing multiples of the sensor signals, dividing linear combinations of the sensor signals. The evaluation device may be configured for using at least one predetermined relationship between the combined signal and the longitudinal coordinate for determining the longitudinal coordinate. The predetermined relationship may be one or more of an empiric relationship, a semi-empiric relationship and an analytically derived relationship. The evaluation device may comprise at least one data storage device for storing the predetermined relationship, such as a lookup list or a lookup table.

The combined signal may be determined by using various means. As an example, a software means for deriving a quotient signal, a hardware means for deriving the quotient signal, or both, may be used and may be implemented in the evaluation device. Thus, the evaluation device, as an example, may comprise at least one divider, wherein the divider is configured for deriving the quotient signal. The divider may fully or partially be embodied as one or both of a software divider or a hardware divider. The divider may fully or partially be integrated into the sensor element answers or may fully or partially be embodied independent from the sensor element.

For example, the combined signal Q, are derived by $$Q(z_o) = \frac{\int\int_{A_1} E(x, y, z_O)dxdy}{\int\int_{A_2} E(x, y, z_O)dxdy}$$

wherein x and y are transversal coordinates, A1 and A2 are different areas of the at least one beam profile at the position of the sensor element of the distance detector, and $E(x,y,z_o)$ denotes a beam profile given at the distance $z_o$. As used herein, the term "beam profile" refers to at least one intensity distribution of a light spot on the optical sensor as a function of the pixel.

The beam profile may be selected from the group consisting of a trapezoid beam profile; a triangle beam profile; a conical beam profile and a linear combination of Gaussian beam profiles.

Area A1 and area A2 may differ. In particular, A1 and A2 are not congruent. Thus, A1 and A2 may differ in one or more of the shape or content. Each of the sensor signals may comprises at least one information of at least one area of the beam profile. Generally the beam profile is dependent on luminance $L(z_o)$ and beam shape $S(x,y;z_o)$, $E(x,y;z_o)=L\cdot S$. Thus, by deriving the combined signal it may allow determining the longitudinal coordinate independent from luminance. In addition, using the combined signal allows determination of the distance $z_o$ independent from an object size. Thus, the combined signal allows determination of the distance $z_o$ independent from the material properties and/or reflective properties and/or scattering properties of the object to be measured and independent from alterations of the light source such as by manufacturing precision, heat, water, dirt, damages on the lens, or the like.

Each of the first sensor signal and the second sensor signal may comprise at least one information of the at least one area of the beam profile. The light-sensitive areas may be arranged such that one of the sensor signals comprises information of a first area of the beam profile and the other one of the sensor signals comprises information of a second area of the beam profile. The first area of the beam profile and the second area of the beam profile may be one or both of adjacent or overlapping regions. The first area and the second area may be not congruent in area. The first area of the beam profile may comprise essentially edge information of the beam profile and the second area of the beam profile may comprise essentially center information of the beam profile. The edge information may comprise information relating to a number of photons in the first area of the beam profile and the center information comprises information relating to a number of photons in the second area of the beam profile. The evaluation device may be configured to determine and/or to select the first area of the beam profile and the second area of the beam profile. The beam profile may have a center, i.e. a maximum value of the beam profile and/or a center point of a plateau of the beam profile and/or a geometrical center of the light spot, and falling edges extending from the center. The second region may comprise inner regions of the cross section and the first region may comprise outer regions of the cross section. As used herein, the term "essentially center information" generally refers to a low proportion of edge information, i.e. proportion of the intensity distribution corresponding to edges, compared to a proportion of the center information, i.e. proportion of the intensity distribution corresponding to the center. Preferably the center information has a proportion of edge information of less than 10%, more preferably of less than 5%, most preferably the center information comprises no edge content. As used herein, the term "essentially edge information" generally refers to a low proportion of center information compared to a proportion of the edge information. The edge information may comprise information of the whole beam profile, in particular from center and edge regions. The edge information may have a proportion of center information of less than 10%, preferably of less than 5%, more preferably the edge information comprises no center content. At least one area of the beam profile may be determined and/or selected as second area of the beam profile if it is close or around the center and comprises essentially center information. At least one area of the beam profile may be determined and/or selected as first area of the beam profile if it comprises at least parts of the falling edges of the cross section. For example, the whole area of the cross section may be determined as first region. The first area of the beam profile may be area A1 and the second area of the beam profile may be area A2.

Other selections of the first area A1 and second area A2 may be feasible. For example, the first area may comprise essentially outer regions of the beam profile and the second area may comprise essentially inner regions of the beam profile. For example, in case of a two-dimensional beam profile, the beam profile may be divided in a left part and a right part, wherein the first area may comprise essentially areas of the left part of the beam profile and the second area may comprise essentially areas of the right part of the beam profile.

The edge information may comprise information relating to a number of photons in the first area of the beam profile and the center information may comprise information relating to a number of photons in the second area of the beam profile. The evaluation device may be adapted for determining an area integral of the beam profile. The evaluation device may be adapted to determine the edge information by integrating and/or summing of the first area. The evaluation device may be adapted to determine the center information by integrating and/or summing of the second area. For example, the beam profile may be a trapezoid beam profile and the evaluation device may be adapted to determine an integral of the trapezoid. Further, when trapezoid beam profiles may be assumed, the determination of edge and center signals may be replaced by equivalent evaluations making use of properties of the trapezoid beam profile such as determination of the slope and position of the edges and of the height of the central plateau and deriving edge and center signals by geometric considerations.

Additionally or alternatively, the evaluation device may be adapted to determine one or both of center information or edge information from at least one slice or cut of the light spot. This may be realized, for example, by replacing the area integrals in the combined signal by a line integral along the slice or cut. For improved accuracy, several slices or cuts through the light spot may be used and averaged. In case of an elliptical spot profile, averaging over several slices or cuts may result in improved distance information.

The evaluation device may be configured for deriving the combined signal by one or more of dividing the respective edge information and the respective center information, dividing multiples of the respective edge information and the respective center information, dividing linear combinations of the respective edge information and the respective center information. Thus, essentially, photon ratios may be used as the physical basis of the depth-from-photon-ratio technique.

As explained, e.g. in WO 2012/110924 A1 or WO 2014/097181 A1, typically, a predetermined or determinable relationship exists between a size of a light spot, such as a diameter of the light spot, a beam waist or an equivalent diameter, and the longitudinal coordinate of the object from which the light beam propagates towards the sensor element of the distance detector. Without wishing to be bound by this theory, the light spot may be characterized by two measurement variables: a measurement signal measured in a small measurement patch in the center or close to the center of the light spot, also referred to as the center signal, and an integral or sum signal integrated over the light spot, with or without the center signal. For a light beam having a certain total power which does not change when the beam is widened or focused, the sum signal should be independent from the spot size of the light spot, and, thus, should, at least when linear optical sensors within their respective measurement range are used, be independent from the distance between the object and the sensor element of the distance detector. The center signal, however, is dependent on the spot size. Thus, the center signal typically increases when the light beam is focused, and decreases when the light beam is defocused. By comparing the center signal and the sum signal, thus, an item of information on the size of the light spot generated by the light beam and, thus, on the longitudinal coordinate of the location of reflection may be generated. The comparing of the center signal and the sum signal, as an example, may be done by forming the combined signal Q out of the center signal and the sum signal and by using a predetermined or determinable relationship between the longitudinal coordinate and the combined signal for deriving the longitudinal coordinate.

The light beam impinging on the optical sensor of the distance detector may fully illuminate the at least one optical sensor of the distance detector from which the center signal is generated, such that the at least one optical sensor from which the center signal arises is fully located within the light beam, with a width of the light beam being larger than the light-sensitive area of the at least one optical sensor of the distance detector from which the sensor signal arises. Contrarily, preferably, the light beam specifically may create a light spot on the entire matrix which is smaller than the matrix, such that the light spot is fully located within the matrix. This situation may easily be adjusted by a person skilled in the art of optics by choosing one or more appropriate lenses or elements having a focusing or defocusing effect on the light beam, such as by using an appropriate transfer device as will be outlined in further detail below. As further used herein, a "light spot" generally refers to a visible or detectable round or non-round illumination.

The combined signal Q may be derived by one or more of: forming a quotient of the first signal and the second signal or vice versa; forming a quotient of a multiple of the first signal and a multiple of the second signal or vice versa; forming a quotient of a linear combination of the first signal and a linear combination of the second signal or vice versa; forming a quotient of a first linear combination of the first signal and the second signal and a second linear combination of the first signal and the second signal. The evaluation device may be configured for using at least one predetermined relationship between the combined signal Q and the longitudinal coordinate z of the object for determining the longitudinal coordinate z. The evaluation device may comprise at least one divider, wherein the divider is configured for deriving the combined signal.

The evaluation device may be adapted to determine those optical sensors of the matrix of optical sensors of the distance detector illuminated by the first wavelength constituent. The evaluation device may be configured for determining the at least one optical sensor of the distance detector illuminated by the first constituent wavelength and having the highest sensor signal and forming the first sensor signal. The first sensor signal may be at least one center signal. The evaluation device may be configured for evaluating the sensor signals of the optical sensors of the matrix illuminated by the first wavelength constituent and forming the second sensor signal. The second sensor signal is at least one sum signal. The evaluation device may be configured for determining the combined signal Q by combining the center signal and the sum signal.

The term "center signal" generally refers to the at least one sensor signal comprising essentially center information of the beam profile. As used herein, the term "highest sensor signal" refers to one or both of a local maximum or a maximum in a region of interest. For example, the center signal may be the signal of the at least one optical sensor and/or pixel of the distance detector having the highest sensor signal out of the plurality of sensor signals generated by the optical sensors and/or pixels of the entire matrix or of a region of interest within the matrix, wherein the region of interest may be predetermined or determinable within an image generated by the optical sensors and/or pixels of the matrix of the distance detector. The center signal may arise from a single optical sensor and/or pixel or from a group of optical sensors, wherein, in the latter case, as an example, the sensor signals of the group of optical sensors and/or pixels may be added up, integrated or averaged, in order to determine the center signal. The group of optical sensors and/or pixels from which the center signal arises may be a group of neighboring optical sensors and/or pixels, such as optical sensors and/or pixels having less than a predetermined distance from the actual optical sensor and/or pixel having the highest sensor signal, or may be a group of optical sensors and/or pixels generating sensor signals being within a predetermined range from the highest sensor signal.

The group of optical sensors and/or pixels from which the center signal arises may be chosen as large as possible in order to allow maximum dynamic range. The evaluation device may be adapted to determine the center signal by integration of the plurality of sensor signals, for example the plurality of optical sensors and/or pixels around the optical sensor and/or pixel having the highest sensor signal.

As outlined above, the center signal generally may be a single sensor signal, such as a sensor signal from the optical sensor and/or pixel of the distance detector in the center of the light spot, or may be a combination of a plurality of sensor signals, such as a combination of sensor signals arising from optical sensors and/or pixels in the center of the light spot, or a secondary sensor signal derived by processing a sensor signal derived by one or more of the aforementioned possibilities. The determination of the center signal may be performed electronically, since a comparison of sensor signals is fairly simply implemented by conventional electronics, or may be performed fully or partially by software. Specifically, the center signal may be selected from the group consisting of: the highest sensor signal; an average of a group of sensor signals being within a predetermined range of tolerance from the highest sensor signal; an average of sensor signals from a group of optical sensors and/or pixels containing the optical sensor and/or pixel having the highest sensor signal and a predetermined group of neighboring optical sensors and/or pixels; a sum of sensor signals from a group of optical sensors and/or pixels containing the optical sensor and/or pixel having the highest sensor signal and a predetermined group of neighboring optical sensors and/or pixels; a sum of a group of sensor signals being within a predetermined range of tolerance from the highest sensor signal; an average of a group of sensor signals being above a predetermined threshold; a sum of a group of sensor signals being above a predetermined threshold; an integral of sensor signals from a group of optical sensors containing the optical sensor having the highest sensor signal and a predetermined group of neighboring optical sensors; an integral of a group of sensor signals being within a predetermined range of tolerance from the highest sensor signal; an integral of a group of sensor signals being above a predetermined threshold.

Similarly, the term "sum signal" generally refers to a signal comprising essentially edge information of the beam profile. For example, the sum signal may be derived by adding up the sensor signals, integrating over the sensor signals or averaging over the sensor signals of the entire matrix or of a region of interest within the matrix of the distance detector, wherein the region of interest may be predetermined or determinable within an image generated by the optical sensors of the matrix. When adding up, integrating over or averaging over the sensor signals, the actual optical sensors from which the sensor signal is generated may be left out of the adding, integration or averaging or, alternatively, may be included into the adding, integration or averaging. The evaluation device may be adapted to determine the sum signal by integrating signals of the entire matrix, or of the region of interest within the matrix. For example, the beam profile may be a trapezoid beam profile and the evaluation device may be adapted to determine an integral of the entire trapezoid. Further, when trapezoid beam profiles may be assumed, the determination of edge and center signals may be replaced by equivalent evaluations making use of properties of the trapezoid beam profile such as determination of the slope and position of the edges and of the height of the central plateau and deriving edge and center signals by geometric considerations.

Similarly, the center signal and edge signal may also be determined by using segments of the beam profile such as circular segments of the beam profile. For example, the beam profile may be divided into two segments by a secant or a chord that does not pass the center of the beam profile. Thus, one segment will essentially contain edge information, while the other segment will contain essentially center information. For example, to further reduce the amount of edge information in the center signal, the edge signal may further be subtracted from the center signal.

Additionally or alternatively, the evaluation device may be adapted to determine one or both of center information or edge information from at least one slice or cut of the light spot. This may be realized for example by replacing the area integrals in the quotient by a line integral along the slice or cut. For improved accuracy, several slices or cuts through the light spot may be used and averaged. In case of an elliptical spot profile, averaging over several slices or cuts may result in an improved distance information.

The center signal is selected from the group consisting of: the highest sensor signal; an average of a group of sensor signals being within a predetermined range of tolerance from the highest sensor signal; an average of sensor signals from a group of optical sensors of the distance detector containing the optical sensor having the highest sensor signal and a predetermined group of neighboring optical sensors; a sum of sensor signals from a group of optical sensors of the distance detector containing the optical sensor having the highest sensor signal and a predetermined group of neighboring optical sensors; a sum of a group of sensor signals being within a predetermined range of tolerance from the highest sensor signal; an average of a group of sensor signals being above a predetermined threshold; a sum of a group of sensor signals being above a predetermined threshold; an integral of sensor signals from a group of optical sensors containing the optical sensor of the distance detector having the highest sensor signal and a predetermined group of neighboring optical sensors; an integral of a group of sensor signals being within a predetermined range of tolerance from the highest sensor signal; an integral of a group of sensor signals being above a predetermined threshold. The sum signal is selected from the group consisting of: an average over all sensor signals of the matrix of the distance detector; a sum of all sensor signals of the matrix of the distance detector; an integral of all sensor signals of the matrix of the distance detector; an average over all sensor signals of the matrix of the distance detector except for sensor signals from those optical sensors of the distance detector contributing to the center signal; a sum of all sensor signals of the matrix of the distance detector except for sensor signals from those optical sensors of the distance detector contributing to the center signal; an integral of all sensor signals of the matrix of the distance detector except for sensor signals from those optical sensors of the distance detector contributing to the center signal; a sum of sensor signals of optical sensors of the distance detector within a predetermined range from the optical sensor of the distance detector having the highest sensor signal; an integral of sensor signals of optical sensors of the distance detector within a predetermined range from the optical sensor of the distance detector having the highest sensor signal; a sum of sensor signals above a certain threshold of optical sensors of the distance detector being located within a predetermined range from the optical sensor of the distance detector having the highest sensor signal; an integral of sensor signals above a certain threshold of optical sensors of the distance detector being located within a predetermined range from the optical sensor of the distance detector having the highest sensor signal.

The combined signal Q may be a signal which is generated by combining the center signal and the sum signal. Specifically, the determining may include one or more of: forming a quotient of the center signal and the sum signal or vice versa; forming a quotient of a multiple of the center signal and a multiple of the sum signal or vice versa; forming a quotient of a linear combination of the center signal and a linear combination of the sum signal or vice versa. Additionally or alternatively, the combined signal Q may comprise an arbitrary signal or signal combination which contains at least one item of information on a comparison between the center signal and the sum signal.

The spectrometer device may be configured for determining at least one spectral or spectroscopic information of the at least one object. The spectrometer device comprises the at least one evaluation device configured for performing at least one spectroscopic analysis considering the determined distance information. The evaluation device may be configured for performing at least one spectroscopic analysis considering the determined longitudinal coordinate z. In the spectroscopic analysis at least one spectral or spectroscopic information of the object may be determined. Specifically, the evaluation device may be configured for determining light attenuation due to the distance between the object and the spectrometer device. As used herein, the term "light attenuation" refers to loss of intensity through travelled pathway of the light beam, i.e. the distance from the object to the spectrometer device, and/or presence of the object and/or ambient conditions. As used herein, the term "determining light attenuation" refers to approximating and/or measuring and/or deriving light attenuation. The spectroscopic analysis may comprise determining at least one difference in at least one light property due to presence of the object. The difference in the light property may be selected from the group consisting of: at least one wavelength dependent intensity difference; at least one wavelength dependent polarization difference. The evaluation device may be adapted to perform the spectroscopic analysis considering the light attenuation. The evaluation device may be adapted to correct intensities of the spectrum of constituent wavelength signals determined by the optical detector. Specifically, the evaluation device may be adapted to correct the determined intensity values for light attenuation, for example by multiplying and/or dividing the determined intensity values with at least one correction function. The correction function may be determined empirically and/or semi-empirically and/or analytically. For example, the spectrometer device may be configured for determining light attenuation by measuring a background spectrum depending on optics, light source, characteristics of light sources, dirt and the like. The spectrometer device may be configured for deriving the correction function, such as a background correction function, therefrom. However, during measuring of the background spectrum the distance between object and spectrometer may be kept fixed. The spectrometer device may be a mobile spectrometer device. Specifically, the distance between the object and the spectrometer device may be variable. The evaluation device may be configured for determining alteration of the distance between the object and the spectrometer device. Thus, the intensity values and/or the background spectrum have to be corrected further for influences due to distance and alteration in distance between object and spectrometer device. The evaluation device may be adapted to correct the determined light attenuation for influences due to the distance between the object and the spectrometer. For correction of light attenuation due to distance a further correction function such as a polynomial correction function, for example a second order or higher order polynomial, may be used. For example, the distance dependent light attenuation may be corrected by a fraction of polynomials in z such as a polynomial up to third order in z divided by a polynomial up to fifth order in z, whereas coefficients may be used to adjust the distance dependent light attenuation function. For example, the correction function may be a rational polynomial function. For example, a polynomial $A \cdot 1/z^2$, with A being a coefficient or constant and z being the longitudinal coordinate z, may be used. The further correction function may be determined considering light emitting characteristics of the illumination source. In addition, the further correction function may be determined by considering per-determined reflection properties of the object, e.g. determined using spot profiles, and/or assumed reflection properties of the object. Further, the correction function may be a combined correction function correcting the light attenuation due to optics, ambient light, dirt, temperature, and correcting the distance dependent light attenuation simultaneously. As an example, the combined correction function may be a product of a distance independent correction function such as a background correction function and a distance dependent correction function.

The spectrometer device may be adapted to determine at least one further longitudinal coordinate of the object by evaluating the combined signal Q from a first sensor signal and a second sensor signal generated in response to a second constituent wavelength. The evaluation device may be adapted to determine a combined longitudinal coordinate, such as a mean value, from the longitudinal coordinate and the further longitudinal coordinate and to perform the spectroscopic analysis considering the combined longitudinal coordinate.

As further used herein, the term "evaluation device" generally refers to an arbitrary device adapted to perform the named operations, preferably by using at least one data processing device and, more preferably, by using at least one processor and/or at least one application-specific integrated circuit. Thus, as an example, the at least one evaluation device may comprise at least one data processing device having a software code stored thereon comprising a number of computer commands. The evaluation device may provide one or more hardware elements for performing one or more of the named operations and/or may provide one or more processors with software running thereon for performing one or more of the named operations.

The above-mentioned operations, including determining the longitudinal coordinate and performing the spectroscopic analysis, are performed by the at least one evaluation device. Thus, as an example, one or more of the above-mentioned relationships may be implemented in software and/or hardware, such as by implementing one or more lookup tables. Thus, as an example, the evaluation device may comprise one or more programmable devices such as one or more computers, application-specific integrated circuits (ASICs), Digital Signal Processors (DSPs), or Field Programmable Gate Arrays (FPGAs) which are configured to perform the above-mentioned evaluation. Additionally or alternatively, however, the evaluation device may also fully or partially be embodied by hardware.

The spectrometer device may be configured for contact-less spectroscopy. Determining the distance information and using the distance information for correction of the spectroscopic measurement allows for variable distances between the object and the spectrometer device. Direct mechanical contact or use of special sample boxes can be avoided.

The evaluation device may be further configured for determining at least one transversal coordinate of the object by evaluating a transversal position of the at least one optical sensor of the distance detector having the highest sensor signal.

As outlined above, the spectrometer device comprises the at least one wavelength selective element, wherein the wavelength selective element is configured for separating incident light into a spectrum of constituent wavelength signals whose respective intensities are determined by employing the spectrum detector. The wavelength selective element is a linear variable filter. The spectrometer device may comprise the at least one tapered light concentrator. The spectrometer device furthermore may comprise at least two illumination sources, wherein each illumination source is configured to illuminate the object by generating and emitting the at least one illumination light beam. The illumination sources may be employed simultaneously or may be employed alternatingly for illumination of the object. The illumination light beam originating from one of the illumination sources may be reflected directly and/or may be scattered from the object. The direct reflection may not be directly distinguishable from the spectral information alone.

The direct reflection may be distance dependent and may be less wavelength dependent than scattered light. The spectrometer device may be adapted to separate the direct reflection and the spectrum of the scattered light by recording at least two spectra at different object distances and/or by recording and comparing at least two spectra using the two light sources alternatingly. The spectrometer device may be adapted to record a spectrum using the two light sources simultaneously.

For example, the illumination sources may be employed alternatingly. For example, firstly, the illumination light beam originating e.g. from a first illumination source may be reflected directly and/or may be scattered from the object at a first distance and the optical sensors of the spectrum detector may be adapted to record at least one first spectrum. Subsequently, the illumination light beam originating from a second illumination source may be reflected directly and/or may be scattered from the object at the first distance and the optical sensors of the spectrum detector may be adapted to record at least one second spectrum. The order or sequence of using the illumination sources is described exemplary only such that other orders of using the illumination sources are possible such as firstly using the second illumination source and subsequently the first illumination source and/or repetitive usage of one or both illumination sources. The spectrometer device, in particular the distance detector, may be configured for determining at least one distance information about a distance between the at least one object and the spectrometer device. By comparing the first spectrum and the second spectrum the evaluation device may be configured for determining at least two direct reflection peaks on the sensor element, specifically a first direct reflection peak originating from direct reflection from the object illuminated by the first illumination source and a second reflection peak originating from direct reflection from the object illuminated by the second illumination source. Specifically, the evaluation device may be configured to determine differences in the intensity distribution as a function of the wavelength, in particular peaks, by comparing the first and the second spectra. The location of the determined peak in the respective spectrum may correspond to a location on the matrix of optical sensors of the distance detector and/or the spectrum detector. The evaluation device may be adapted to determine a location at which the directly reflected light impinges on the matrix of optical sensors. For example, the evaluation device may be adapted to determine a location at which the directly reflected light originating from the object at the first distance illuminated by the first illumination source impinges on the matrix of optical sensors. The evaluation device may be adapted to determine a location at which the directly reflected light originating from the object at the first distance illuminated by the second illumination source impinges on the matrix of optical sensors. As outlined above, the direct reflection may be distance dependent and may be less wavelength dependent than scattered light. Once the locations on which the directly reflected light impinges on the matrix of optical sensors are known, triangulation algorithms can be used to determine the distance information about the first distance between the spectrometer device and the object. The evaluation device may be adapted to determine the first distance of the object by using at least one triangulation algorithm.

For example, the illumination sources may be employed simultaneously. The illumination light beam originating e.g. from the first illumination source may be reflected directly and/or may be scattered from the object at the first distance. The second illumination source may be employed for illuminating the object. The illumination light beam originating from the second illumination source may be reflected directly and/or may be scattered from the object at the first distance. The optical sensors of the spectrum detector may be adapted to record the at least one first spectrum of the received light for the object at the first distance. Recording of the spectrum is repeated for a second distance of the object. The illumination light beam originating e.g. from the first illumination source may be reflected directly and/or may be scattered from the object at the second distance. The illumination light beam originating from the second illumination source may be reflected directly and/or may be scattered from the object at the second distance. The optical sensors of the spectrum detector may be adapted to record the at least one first spectrum of the received light for the object at the second distance. By comparing the first spectrum and the second spectrum the evaluation device may be configured for determining at least four direct reflection peaks on the sensor element. Specifically, the evaluation device may be adapted to determine in the first spectrum a first direct reflection peak originating from direct reflection from the object illuminated by the first illumination source and a second reflection peak originating from direct reflection from the object illuminated by the second illumination source. Specifically, the evaluation device may be adapted to determine in the second spectrum a third direct reflection peak originating from direct reflection from the object illuminated by the first illumination source and a fourth reflection peak originating from direct reflection from the object illuminated by the second illumination source. The evaluation device may be configured to determine differences in the intensity distribution as a function of the wavelength, in particular peaks, by comparing the first and the second spectra. The location of the determined peak in the respective spectrum may correspond to a location on the matrix of optical sensors of the distance detector and/or spectrum detector. Specifically, the evaluation device may be adapted to determine the locations at which the directly reflected light impinges on the matrix of optical sensors. For example, the reflected light originates from the object at the first distance and the second distance and the evaluation device may be adapted to determine the location at which the directly reflected light originating from the object at the first distance illuminated by the first illumination source impinges on the matrix of optical sensors. The evaluation device may be adapted to determine the location at which the directly reflected light originating from the object at the first distance illuminated by the second illumination source impinges on the matrix of optical sensors. The evaluation device may be adapted to determine a location at which the directly reflected light originating from the object at the second distance illuminated by the first illumination source impinges on the matrix of optical sensors. The evaluation device may be adapted to determine a location at which the directly reflected light originating from the object at the first distance illuminated by the second illumination source impinges on the matrix of optical sensors. Once at least two locations corresponding to the same object distance of the locations at which the direct reflection impinges on the matrix are known, triangulation algorithms can be used to determine the distance information about the distance between the spectrometer device and the object. The evaluation device may be adapted to determine the distance to the object by using at least one triangulation algorithm.

The evaluation device is configured for determining material information of the object by evaluating of at least one image of the object determined by at least one pixelated imaging detector configured for determining at least one image of the object. As used herein, the term "material information" refers to arbitrary information about the material of the object configured for characterizing and/or identification and/or classification of the material. For example, the material information may be at least one property selected from the group consisting of: a scattering coefficient, a translucency, a transparency, a deviation from a Lambertian surface reflection, a speckle, material and/or material class; object type and/or object class, and the like. The material information may comprise information about a material property. As used herein, the term "material property" refers to at least one arbitrary property of the material configured for characterizing and/or identification and/or classification of the material. For example, the material property may be a property selected from the group consisting of: roughness, penetration depth of light into the material, a property characterizing the material as biological or non-biological material, a reflectivity, a specular reflectivity, a diffuse reflectivity, a surface property, a measure for translucence, a scattering, specifically a back-scattering behavior or the like. The at least one material property may be a property selected from the group consisting of: a scattering coefficient, a translucency, a transparency, a deviation from a Lambertian surface reflection, a speckle, and the like.

As used herein, the term "determining material information" refers to one or more of determining and assigning the material property to the object. The evaluation device may comprise at least one database comprising a list and/or table, such as a lookup list or a lookup table, of predefined and/or predetermined material information. The list and/or table of material information may be determined and/or generated by performing at least one test measurement using the spectrometer according to the present invention, for example by performing material tests using samples having known material properties. The list and/or table of material information may be determined and/or generated at the manufacturer site and/or by the user of the spectrometer device. The material information may additionally be assigned to a material classifier such as one or more of a material name, a material group such as biological or non-biological material, translucent or non-translucent materials, metal or non-metal, skin or non-skin, fur or non-fur, carpet or non-carpet, reflective or non-reflective, specular reflective or non-specular reflective, foam or non-foam, hair or non-hair, roughness groups or the like. The evaluation device may comprise at least one database comprising a list and/or table comprising the material information and associated material name and/or material group.

The "object" may, generally, be an arbitrary sample of interest. The sample may be a liquid sample or a solid sample. The object may comprise one or more articles and/or one or more parts of an article, wherein the at least one article or the at least one part thereof may comprise at least one component which may provide a spectrum suitable for investigations. Additionally or alternatively, the object may be or may comprise one or more living beings and/or one or more parts thereof, such as one or more body parts or bodily fluids of a human being, e.g. a user, or of an animal. For example, the object may be at least one object selected from the group consisting of: a scene, a human such as a human, wood, carpet, foam, an animal such as a cow, a plant, a piece of tissue, a metal, a toy, a metallic object, a beverage, a food such as a fruit, meat, fish, a dish, a cosmetics product, an applied cosmetics product, cloth, fur, hair, a maintenance product, a cream, an oil, a powder, a carpet, a juice, a suspension, a paint, a plant, a body, a part of a body, organic material, inorganic material, a reflective material, a screen, a display, a wall, a sheet of paper, such as photograph. The object may comprise at least one surface on which the illumination is projected. The surface may be adapted to at least partially reflect the illumination towards the spectrometer device. For example, without wishing to be bound by this theory, human skin may have a reflection profile, also denoted back scattering profile, comprising parts generated by back reflection of the surface, denoted as surface reflection, and parts generated by very diffuse reflection from light penetrating the skin, denoted as diffuse part of the back reflection. With respect to reflection profile of human skin reference is made to "Lasertechnik in der Medizin: Grundlagen, Systeme, Anwendungen", "Wirkung von Laserstrahlung auf Gewebe", 1991, pages 171 to 266, Jürgen Eichler, Theo Seiler, Springer Verlag, ISBN 0939-0979. The surface reflection of the skin may increase with the wavelength increasing towards the near infrared. Further, the penetration depth may increase with increasing wavelength from visible to near infrared. The diffuse part of the back reflection may increase with penetrating depth of the light. These material properties may be used to distinguish skin from other materials, specifically by analyzing the back scattering profile.

Specifically, the spectrometer device may be configured for detection of biological tissue, in particular human skin. As used herein, the term "biological tissue" generally refers to biological material comprising living cells. The spectrometer device may be a device for detection, in particular optical detection, of biological tissue, in particular of human skin. The term "detection of biological tissue" refers to determining and/or validating whether a surface to be examined or under test is or comprises biological tissue, in particular human skin, and/or to distinguish biological tissue, in particular human skin, from other tissues, in particular other surfaces, and/or distinguishing different types of biological tissue such as distinguishing different types of human tissue e.g. muscle, fat, organs, or the like. For example, the biological tissue may be or may comprise human tissue or parts thereof such as skin, hair, muscle, fat, organs, or the like. For example, the biological tissue may be or may comprise animal tissue or a part thereof such as skin, fur, muscle, fat, organs, or the like. For example, the biological tissue may be or may comprise plant tissue or a part thereof. The spectrometer device may be adapted to distinguish animal tissue or parts thereof from one or more of inorganic tissue, metal surfaces, plastics surfaces, for example of farming machines or milking machines. The spectrometer device may be adapted to distinguish plant tissue or parts thereof from one or more of inorganic tissue, metal surfaces, plastics surfaces, for example of farming machines. The spectrometer device may be adapted to distinguish food and/or beverage from dish and/or glasses. The spectrometer device may be adapted to distinguish different types of food such as a fruit, meat, and fish. The spectrometer device may be adapted to distinguish a cosmetics product and/or, an applied cosmetics product from human skin. The spectrometer device may be adapted to distinguish human skin from foam, paper, wood, a display, a screen. The spectrometer device may be adapted to distinguish human skin from cloth. The spectrometer device may be adapted to distinguish a maintenance product from material of machine components such metal components etc. The spectrometer device may be adapted to distinguish organic material from inorganic material. The spectrometer device may be adapted to distinguish human biological tissue from surfaces of artificial or non-living objects. The spectrometer device may be used, in particular, for non-therapeutic and non-diagnostic applications.

The evaluation device may be configured for determining the material information by applying at least one material dependent image filter $\Phi$ to the image of the object determined by the pixelated imaging detector. Specifically, the evaluation device may be configured for determining at least one material feature $\varphi_m$ by applying the material dependent image filter $\Phi$ to the image of the object determined by the imaging detector.

The material dependent image filter may be at least one filter selected from the group consisting of: a luminance filter; a spot shape filter; a squared norm gradient; a standard deviation; a smoothness filter such as a Gaussian filter or median filter; a grey-level-occurrence-based contrast filter; a grey-level-occurrence-based energy filter; a grey-level-occurrence-based homogeneity filter; a grey-level-occurrence-based dissimilarity filter; a Law's energy filter; a threshold area filter; or a linear combination thereof; or a further material dependent image filter $\Phi_{other}$ which correlates to one or more of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof by $|\rho_{\Phi other,\Phi m}| \geq 0.40$ with $\Phi_m$ being one of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof.

As used herein, the term "image of the object" refers to an image determined by the pixelated imaging detector comprising at least one object feature such as a reflection feature. As furthermore used herein, without limitation, the term "image" specifically may relate to data recorded by using the imaging detector, such as a plurality of electronic readings from an imaging device, such as the pixels of the pixelated optical detector. The image itself, thus, may comprise pixels, the pixels of the image correlating to pixels of the pixelated optical detector. Consequently, when referring to "pixels", reference is either made to the units of image information generated by the single pixels of the pixelated optical detector or to the single pixels of the pixelated optical detector directly. As used herein, the term "reflection feature" refers to a feature in an image plane generated by the object in response to illumination, for example with at least one illumination feature. In particular, the imaging detector may be configured for determining and/or imaging and/or recording the image of the object.

The least one light beam may propagate from the object towards the spectrometer device. The light beam may originate from the object or may originate from an illumination source, such as from an illumination source directly or indirectly illuminating the object, wherein the light beam is reflected or scattered by the object and, thereby, is at least partially directed towards the detector. The spectrometer device may be used in active and/or passive illumination scenarios. For example, the at least one illumination source may be adapted to illuminate the object, for example, by directing a light beam towards the object, which reflects the light beam. Additionally or alternatively to the at least one illumination source, the spectrometer device may use radiation already present in the scene such as from at least one ambient light source.

The imaging detector may be configured for recording a beam profile of at least one reflection feature of the image of the object. The evaluation device may be configured for identifying and/or selecting the at least one reflection feature in the image, specifically at least one light spot, provided by the imaging detector. The evaluation device may be configured for performing at least one image analysis and/or image processing in order to identify the reflection feature. The image analysis and/or image processing may use at least one feature detection algorithm. The image analysis and/or image processing may comprise one or more of the following: a filtering; a selection of at least one region of interest; a formation of a difference image between an image created by the sensor signals and at least one offset; an inversion of sensor signals by inverting an image created by the sensor signals; a formation of a difference image between an image created by the sensor signals at different times; a background correction; a decomposition into color channels; a decomposition into hue; saturation; and brightness channels; a frequency decomposition; a singular value decomposition; applying a blob detector; applying a corner detector; applying a Determinant of Hessian filter; applying a principle curvature-based region detector; applying a maximally stable extremal regions detector; applying a generalized Hough-transformation; applying a ridge detector; applying an affine invariant feature detector; applying an affine-adapted interest point operator; applying a Harris affine region detector; applying a Hessian affine region detector; applying a scale-invariant feature transform; applying a scale-space extrema detector; applying a local feature detector; applying speeded up robust features algorithm; applying a gradient location and orientation histogram algorithm; applying a histogram of oriented gradients descriptor; applying a Deriche edge detector; applying a differential edge detector; applying a spatio-temporal interest point detector; applying a Moravec corner detector; applying a Canny edge detector; applying a Laplacian of Gaussian filter; applying a Difference of Gaussian filter; applying a Sobel operator; applying a Laplace operator; applying a Scharr operator; applying a Prewitt operator; applying a Roberts operator;

applying a Kirsch operator; applying a high-pass filter; applying a low-pass filter; applying a Fourier transformation; applying a Radon-transformation; applying a Hough-transformation; applying a wavelet-transformation; a thresholding; creating a binary image. Specifically, the evaluation of the image comprises selecting the region of interest in the image. The region of interest may be determined manually by a user or may be determined automatically, such as by recognizing an object within an image generated by the sensor element. For example, in case of a spot-like reflection feature the region of interest may be selected as a region around the spot profile.

For example, the illumination source may be adapted to generate and/or to project a cloud of points such that a plurality of illuminated regions is generated on the matrix of optical sensors, for example the CMOS detector. Additionally, disturbances may be present on the matrix of optical sensors of the imaging detector such as disturbances due to speckles and/or extraneous light and/or multiple reflections. The evaluation device may be adapted to determine at least one region of interest, for example one or more pixels illuminated by the light beam which are used for determination of the longitudinal coordinate of the object. For example, the evaluation device may be adapted to perform a filtering method, for example, a blob-analysis and/or an edge filter and/or object recognition method.

The evaluation device may be configured for performing at least one image correction. The image correction may comprise at least one background subtraction. The evaluation device may be adapted to remove influences from background light from the reflection beam profile, for example, by an imaging without further illumination.

The evaluation device may be configured for determining the material information by evaluating the beam profile of the image of the object. As used herein, the term "beam profile of the image" refers to at least one intensity distribution of at least one of the reflection features of the image, such as of a light spot on the sensor element, as a function of the pixel. The beam profile of the image, also denoted reflection beam profile, may be selected from the group consisting of a trapezoid beam profile; a triangle beam profile; a conical beam profile and a linear combination of Gaussian beam profiles. As used herein, the term "evaluating the beam profile" refers to applying at least one material dependent image filter to the beam profile and/or to at least one specific region of the beam profile.

As used herein, the term "image" refers to a two-dimensional function, f(x,y), wherein brightness and/or color values are given for any x,y-position in the image. The position may be discretized corresponding to the recording pixels. The brightness and/or color may be discretized corresponding to a bit-depth of the optical sensors. As used herein, the term "image filter" refers to at least one mathematical operation applied to the beam profile and/or to the at least one specific region of the beam profile. Specifically, the image filter $\Phi$ maps an image f, or a region of interest in the image, onto a real number, $\Phi(f(x,y))=\varphi$, wherein $\varphi$ denotes a feature, in particular a material feature in case of material dependent image filters. Images may be subject to noise and the same holds true for features. Therefore, features may be random variables. The features may be normally distributed. If features are not normally distributed, they may be transformed to be normally distributed such as by a Box-Cox-Transformation.

The evaluation device may be configured for determining at least one material feature $\varphi_m$ by applying at least one material dependent image filter $\Phi$ to the image. As used herein, the term "material dependent" image filter refers to an image filter having a material dependent output. The output of the material dependent image filter is denoted herein "material feature $\varphi_m$" or "material dependent feature $\varphi_m$". The material feature may be or may comprise the material information.

The material dependent image filter may be at least one filter selected from the group consisting of: a luminance filter; a spot shape filter; a squared norm gradient; a standard deviation; a smoothness filter such as a Gaussian filter or median filter; a grey-level-occurrence-based contrast filter; a grey-level-occurrence-based energy filter; a grey-level-occurrence-based homogeneity filter; a grey-level-occurrence-based dissimilarity filter; a Law's energy filter; a threshold area filter; or a linear combination thereof; or a further material dependent image filter mother which correlates to one or more of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof by $|\rho_{\Phi other,\Phi m}| \geq 0.40$ with $\Phi_m$ being one of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof. The further material dependent image filter $\Phi_{other}$ may correlate to one or more of the material dependent image filters $\Phi_m$ by $|\rho_{\Phi other,\Phi m}| \geq 0.60$, preferably by $|\rho_{\Phi other,\Phi m}| \geq 0.80$.

The similarity of two image filters $\Phi_i$ and $\Phi_j$ may be assessed through the correlation of their features, specifically, by calculating Pearson's correlation coefficients, $$\rho_{\Phi_i \Phi_j} = \frac{\text{cov}((\Phi_i(f(x,y)) - \mu_i)(\Phi_j(f(x,y)) - \mu_j))}{\sigma_i \sigma_j},$$

wherein $\mu$ and $\sigma$ are mean value and standard deviation of the obtained features.

The material dependent image filter may be at least one arbitrary filter $\Phi$ that passes a hypothesis testing. As used herein, the term "passes a hypothesis testing" refers to the fact that a Null-hypothesis $H_0$ is rejected and an alternative hypothesis $H_1$ is accepted. The hypothesis testing may comprise testing the material dependency of the image filter by applying the image filter to a predefined data set. The data set may comprise a plurality of beam profile images. As used herein, the term "beam profile image" refers to a sum of $N_B$ Gaussian radial basis functions, $$f_k(x,y) = \left| \sum_{l=0}^{N_B-1} g_{lk}(x,y) \right|,$$

$$g_{lk}(x,y) = a_{lk} e^{-(\alpha(x-x_{lk}))^2} e^{-(\alpha(y-y_{lk}))^2}$$

wherein each of the $N_B$ Gaussian radial basis functions is defined by a center $(x_{lk}, y_{lk})$, a prefactor, $a_{lk}$, and an exponential factor $\alpha=1/\epsilon$. The exponential factor is identical for all Gaussian functions in all images. The center-positions, $x_{lk}, y_{lk}$, are identical for all images $f_k$: $(x_0, x_1, \ldots, x_{N_B-1})$, $(y_0, y_1, \ldots, y_{N_B-1})$. Each of the beam profile images in the dataset may correspond to a material classifier and a distance. The material classifier may be a label such as 'Material A', 'Material B', etc. The beam profile images may be generated by using the above formula for $f_k(x,y)$ in combination with the following parameter table:

| Image Index | Material classifier, Material Index | Distance z | Parameters |
|---|---|---|---|
| k = 0 | Skin, m = 0 | 0.4 m | $(a_{00}, a_{10}, \ldots, a_{N_B-10})$ |
| k = 1 | Skin, m = 0 | 0.6 m | $(a_{01}, a_{11}, \ldots, a_{N_B-11})$ |
| k = 2 | Fabric, m = 1 | 0.6 m | $(a_{02}, a_{12}, \ldots, a_{N_B-12})$ |
| . | . | . | |
| . | . | . | |
| . | . | . | |
| k = N | Material J, m = J − 1 | | $(a_{0N}, a_{1N}, \ldots, a_{N_B-1N})$ |

The values for x, y, are integers corresponding to pixels with $$\binom{x}{y}$$

$\in [0, 1, \ldots 31]^2$. The images may have a pixel size of 32×32. The dataset of beam profile images may be generated by using the above formula for $f_k$ in combination with a parameter set to obtain a continuous description of $f_k$. The values for each pixel in the 32×32-image may be obtained by inserting integer values from $0, \ldots, 31$ for x, y, in $f_k(x, y)$. For example, for pixel (6,9), the value $f_k(6,9)$ may be computed.

Subsequently, for each image $f_k$, the feature value $\varphi_k$ corresponding to the filter $\Phi$ may be calculated, $\Phi(f_k(x,y), z_k)=\varphi_k$, wherein $z_k$ is a distance value corresponding to the image $f_k$ from the predefined data set. This yields a dataset with corresponding generated feature values $\varphi_k$.

The hypothesis testing may use a Null-hypothesis that the filter does not distinguish between material classifier. The Null-Hypothesis may be given by $H_0: \mu_1=\mu_2=\ldots=\mu_J$, wherein $\mu_m$ is the expectation value of each material-group corresponding to the feature values $\varphi_k$. Index m denotes the material group. The hypothesis testing may use as alternative hypothesis that the filter does distinguish between at least two material classifiers. The alternative hypothesis may be given by $H_1: \exists m, m': \mu_m \neq \mu_{m'}$. As used herein, the term "not distinguish between material classifiers" refers to that the expectation values of the material classifiers are identical. As used herein, the term "distinguishes material classifiers" refers to that at least two expectation values of the material classifiers differ. As used herein "distinguishes at least two material classifiers" is used synonymous to "suitable material classifier". The hypothesis testing may comprise at least one analysis of variance (ANOVA) on the generated feature values. In particular, the hypothesis testing may comprise determining a mean-value of the feature values for each of the J materials, i.e. in total J mean values, $$\bar{\varphi}_m = \frac{\Sigma_i \varphi_{i,m}}{N_m},$$

for $m \in [0, 1, \ldots, J-1]$, wherein $N_m$ gives the number of feature values for each of the J materials in the predefined data set. The hypothesis testing may comprise determining a mean-value of all N feature values $$\bar{\varphi} = \frac{\Sigma_m \Sigma_i \varphi_{i,m}}{N}.$$

The hypothesis testing may comprise determining a Mean Sum Squares within:

$$mssw=(\Sigma_m \Sigma_i (\varphi_{i,m}-\bar{\varphi})^2)(N-J).$$

The hypothesis testing may comprise determining a Mean Sum of Squares between, $$mssb=(\Sigma_m (\bar{\varphi}_m-\bar{\varphi})^2 N_m)/(J-1).$$

The hypothesis testing may comprise performing an F-Test:

$$CDF(x) = I_{\frac{d_1 x}{d_1 x + d_2}}\left(\frac{d_1}{2}, \frac{d_2}{2}\right),$$

where $d_1=N-J$, $d_2=J-1$,
$F(x)=1-CDF(x)$
$p=F(mssb/mssw)$
Herein, $I_x$ is the regularized incomplete Beta-Function, $$I_x(a, b) = \frac{B(x; a, b)}{B(a, b)},$$

with the Euler Beta-Function $B(a, b)=\int_0^1 t^{a-1}(1-t)^{b-1}dt$ and $B(x; a, b)=\int_0^x t^{a-1}(1-t)^{b-1}dt$ being the incomplete Beta-Function. The image filter may pass the hypothesis testing if a p-value, p, is smaller or equal than a pre-defined level of significance. The filter may pass the hypothesis testing if $p \leq 0.075$, preferably $p \leq 0.05$, more preferably $p \leq 0.025$, and most preferably $p \leq 0.01$. For example, in case the pre-defined level of significance is $\alpha=0.075$, the image filter may pass the hypothesis testing if the p-value is smaller than $\alpha=0.075$. In this case the Null-hypothesis $H_0$ can be rejected and the alternative hypothesis $H_1$ can be accepted. The image filter thus distinguishes at least two material classifiers. Thus, the image filter passes the hypothesis testing.

In the following, image filters are described assuming that the reflection image comprises at least one reflection feature, in particular a spot image. A spot image $f$ may be given by a function $f: \mathbb{R}^2 \to \mathbb{R}_{\geq 0}$, wherein the background of the image f may be already subtracted. However, other reflection features may be possible.

For example, the material dependent image filter may be a luminance filter. The luminance filter may return a luminance measure of a spot as material feature. The material feature may be determined by $$\varphi_m = \Phi(f, z) = -\int f(x)dx \frac{z^2}{d_{ray} \cdot n},$$

where f is the spot image. The distance of the spot is denoted by z, where z may be obtained for example by using a depth-from-defocus or depth-from-photon ratio technique and/or by using a triangulation technique. The surface normal of the material is given by $n \in \mathbb{R}^3$ and can be obtained as the normal of the surface spanned by at least three measured points. The vector $d_{ray} \in \mathbb{R}^3$ is the direction vector of the light source. Since the position of the spot is known by using a depth-from-defocus or depth-from-photon ratio technique and/or by using a triangulation technique wherein the position of the light source is known as a parameter of the detector system, $d_{ray}$, is the difference vector between spot and light source positions.

For example, the material dependent image filter may be a filter having an output dependent on a spot shape. This material dependent image filter may return a value which correlates to the translucence of a material as material feature. The translucence of materials influences the shape of the spots. The material feature may be given by $$\varphi_m = \Phi(f) = \frac{\int H(f(x) - \alpha h) dx}{\int H(f(x) - \beta h) dx},$$

wherein $0<\alpha, \beta<1$ are weights for the spot height h, and H denotes the Heavyside function, i.e. H(x)=1: x≥0, H(x)=0: x<0. The spot height h may be determined by $$h = \int_{B_r} f(x) dx,$$

where $B_r$ is an inner circle of a spot with radius r.

For example, the material dependent image filter may be a squared norm gradient. This material dependent image filter may return a value which correlates to a measure of soft and hard transitions and/or roughness of a spot as material feature. The material feature may be defined by $$\varphi_m = \Phi(f) = \int \|\nabla f(x)\|^2 dx.$$

For example, the material dependent image filter may be a standard deviation. The standard deviation of the spot may be determined by $$\varphi_m = \Phi(f) = \int (f(x) - \mu)^2 dx,$$

Wherein $\mu$ is the mean value given by $\mu = \int (f(x)) dx$.

For example, the material dependent image filter may be a smoothness filter such as a Gaussian filter or median filter. In one embodiment of the smoothness filter, this image filter may refer to the observation that volume scattering exhibits less speckle contrast compared to diffuse scattering materials. This image filter may quantify the smoothness of the spot corresponding to speckle contrast as material feature. The material feature may be determined by $$\varphi_m = \Phi(f, z) = \frac{\int |\mathcal{F}(f)(x) - f(x)| dx}{\int f(x) dx} \cdot \frac{1}{z},$$

wherein $\mathcal{F}$ is a smoothness function, for example a median filter or Gaussian filter. This image filter may comprise dividing by the distance z, as described in the formula above. The distance z may be determined for example using a depth-from-defocus or depth-from-photon ratio technique and/or by using a triangulation technique. This may allow the filter to be insensitive to distance. In one embodiment of the smoothness filter, the smoothness filter may be based on the standard deviation of an extracted speckle noise pattern. A speckle noise pattern N can be described in an empirical way by $$f(x) = f_0(x) \cdot (N(X) + 1),$$

where $f_0$ is an image of a despeckled spot. N(X) is the noise term that models the speckle pattern. The computation of a despeckled image may be difficult. Thus, the despeckled image may be approximated with a smoothed version of f, i.e. $f_0 \approx \mathcal{F}(f)$, wherein $\mathcal{F}$ is a smoothness operator like a Gaussian filter or median filter. Thus, an approximation of the speckle pattern may be given by $$N(X) = \frac{f(x)}{\mathcal{F}(f(x))} - 1.$$

The material feature of this filter may be determined by $$\varphi_m = \Phi(f) = \sqrt{\text{Var}\left(\frac{f}{\mathcal{F}(f)} - 1\right)},$$

Wherein Var denotes the variance function.

For example, the image filter may be a grey-level-occurrence-based contrast filter. This material filter may be based on the grey level occurrence matrix $M_{f,\rho}(g_1 g_2) = [p_{g_1,g_2}]$, whereas $p_{g_1,g_2}$ is the occurrence rate of the grey combination $(g_1,g_2)=[f(x_1,y_1),f(x_2,y_2)]$, and the relation $\rho$ defines the distance between $(x_1,y_1)$ and $(x_2,y_2)$, which is $\rho(x,y)=(x+a, y+b)$ with a and b selected from 0,1.

The material feature of the grey-level-occurrence-based contrast filter may be given by $$\varphi_m = \Phi(f) = \sum_{i,j=0}^{N-1} p_{ij}(i-j)^2.$$

For example, the image filter may be a grey-level-occurrence-based energy filter. This material filter is based on the grey level occurrence matrix defined above.

The material feature of the grey-level-occurrence-based energy filter may be given by $$\varphi_m = \Phi(f) = \sum_{i,j=0}^{N-1} (p_{ij})^2.$$

For example, the image filter may be a grey-level-occurrence-based homogeneity filter. This material filter is based on the grey level occurrence matrix defined above.

The material feature of the grey-level-occurrence-based homogeneity filter may be given by $$\varphi_m = \Phi(f) = \sum_{i,j=0}^{N-1} \frac{p_{ij}}{1+|i-j|}.$$

For example, the image filter may be a grey-level-occurrence-based dissimilarity filter. This material filter is based on the grey level occurrence matrix defined above.

The material feature of the grey-level-occurrence-based dissimilarity filter may be given by $$\varphi_m = \Phi(f) = -\sum_{i,j=0}^{N-1} \sqrt{p_{ij} \log(p_{ij})}.$$

For example, the image filter may be a Law's energy filter. This material filter may be based on the laws vector $L_5=[1, 4,6,4,1]$ and $E_5=[-1,-2,0,-2,-1]$ and the matrices $L_5(E_5)^T$ and $E_5(L_5)^T$.

The image $f_k$ is convoluted with these matrices:

$$f^*_{kL5E5}(x, y) = \sum_{i=-2}^{2}\sum_{j=-2}^{2} f_k(x+i, y+j)L_5(E_5)^T$$

and $$f^*_{kE5L5}(x, y) = \Sigma_{i=-2}^{2}\Sigma_{j=-2}^{2} f_k(x+i, y+j)E_5(L_5)^T.$$

$$E = \int \frac{f^*_{kL5E5}(x, y)}{\max(f^*_{kL5E5}(x, y))} dx dy,$$

$$F = \int \frac{f^*_{kE5L5(x,y)}}{\max(f^*_{kE5L5(x,y)})} dx dy,$$

Whereas the material feature of Law's energy filter may be determined by $$\varphi_m = \Phi(f) = E/F.$$

For example, the material dependent image filter may be a threshold area filter. This material feature may relate two areas in the image plane. A first area $\Omega 1$, may be an area wherein the function f is larger than $\alpha$ times the maximum of f. A second area $\Omega 2$, may be an area wherein the function f is smaller than $\alpha$ times the maximum of f, but larger than a threshold value $\varepsilon$ times the maximum of f. Preferably $\alpha$ may be 0.5 and $\varepsilon$ may be 0.05. Due to speckles or noise, the areas may not simply correspond to an inner and an outer circle around the spot center. As an example, $\Omega 1$ may comprise speckles or unconnected areas in the outer circle. The material feature may be determined by $$\varphi_m = \Phi(f) = \frac{\int_{\Omega 1} 1}{\int_{\Omega 2} 1},$$

wherein $\Omega 1 = \{x|f(x) > \alpha \cdot \max(f(x))\}$ and $\Omega 2 = \{x|\varepsilon \cdot \max(f(x)) < f(x) < \alpha \cdot \max(f(x))\}$.

The material information m may be determined by using a predetermined relationship between $\varphi_m$ and m. The evaluation device may be configured for using at least one predetermined relationship between the material feature $\varphi_m$ and the material information of the object for determining the material information of the object. The predetermined relationship may be one or more of an empirical relationship, a semi-empiric relationship and an analytically derived relationship. The evaluation device may comprise at least one data storage device for storing the predetermined relationship, such as a lookup list or a lookup table.

In the ideal case, an image filter would yield features that are only dependent on material properties. However, image filters used in beam profile analysis may yield features that depend on distance and material properties, such as translucency. At least one of the material dependent image filter may be a function of the distance. The evaluation device may be configured for determining whether the used material dependent image filter is a function of the distance. Specifically, the evaluation device may be configured for determining a correlation coefficient of the material dependent image filter and the method used for determining the distance information. In case the correlation coefficient of the material dependent image filter with the method used for determining the distance information is close to 1 or −1, the distance may be projected out, by projecting the material feature on the principal axis with the lowest variance. As an example, the material feature may be projected onto an axis orthogonal to the correlating main component. In other words, the material feature may be projected onto the second main component. This may be done using a principal component analysis as known to the person skilled in the art.

The material information may be determined by evaluating $\varphi_m$ subsequently after determining of the longitudinal coordinate z such that the information about the longitudinal coordinate z can be considered for evaluating of $\varphi_m$. Specifically, the material information m may be determined by a function $m(z, \varphi_m)$. The function may be predefined and/or predetermined. For example, the function may be a linear function.

Additionally or alternatively, the evaluation device may be configured for determining the material information by one or more of: comparative image analysis such as based on comparison the image of the object to an object library; material property analysis such as by comparison of parameters determined from the image of the object 112 to a database with stored parameters such as color, translucency, state of matter or the like. The evaluation device may comprise at least one database comprising the object library and/or stored parameters such as a list and/or table of possible objects and possible parameters, such as a lookup list or a lookup table. The object library may comprise images of different objects to which the determined image of the object can be compared. The evaluation device may be configured for determining via image analysis at least one parameter of the object such as reflectivity, color, translucency, state such as liquid or solid, roughness and the like.

The optical sensors for determining the distance information and/or the optical sensors used for spectroscopy and/or the optical sensors for imaging the object may be identical. Specifically, the optical sensors for determining the distance information may be used for imaging the object and/or for spectroscopy or the other way round. Thus, the optical sensors for determining the distance information and/or used for spectroscopy may correspond to or may be designed as the optical sensors for imaging the object.

The evaluation device may be configured for performing at least one spectroscopic analysis of the determined intensities considering the determined distance information and the material information. The material information may be used for pre-classifying the object, specifically before performing the spectroscopic analysis, in particular before performing the spectroscopic measurement and/or the evaluation of the determined spectrum. The spectrometer device may be configured for selecting at least one analyte of interest depending on the material information and may perform the spectroscopic measurement for the selected analyte of interest. Additionally or alternatively, the material information may be used as input parameter for the evaluation of the determined spectrum which may allow speeding up the evaluation.

The spectrometer device may comprise at least one display device configured for displaying the material information. The displaying of the material information may comprise arbitrary form of presentation such as graphically displaying the material information. The display device may, e.g. additionally, be configured for displaying a suggestion for the kind of material or product the object may be. As an example, the material information may be "a white liquid" or "white translucent liquid" and the display device may display a list of suggestions such as paint, milk, cream, yoghurt, dough, starch, or the like.

The spectrometer device may be configured for selecting at least one analyte of interest depending on the material information. For example, the evaluation device may comprise a database in which material information and associated analytes of interests are stored. The display device may provide the list of potential analytes of interest. The spectrometer device may comprise at least one human-machine interface configured to permit a user to select at least one analyte of the list. The spectrometer device may be configured to perform at least one spectroscopic analysis for the selected analyte of interest. Thus, it may be possible to allow providing material information of the sample, specifically, before determining the spectroscopic information, in order to facilitate the application for the user. As an example, the spectrometer device may allow detecting whether a sample is milk, in order to display the fat or lactose content.

In a further aspect, the present invention discloses a method for determining at least one difference in at least one light property of at least one light beam originating from at least one object. In the method, at least one spectrometer device according to the present invention, such as according to one or more of the embodiments referring to a spectrometer device as disclosed above or as disclosed in further detail below is used. Still, other types of spectrometer devices may be used. The method comprises the following method steps, wherein the method steps may be performed in the given order or may be performed in a different order. Further, one or more additional method steps may be present which are not listed. Further, one, more than one or even all of the method steps may be performed repeatedly.

The method steps are as follows:
  determining intensities of constituent wavelength signals of at least one light beam propagating from the object to the spectrometer device;
  determining at least one distance information between at least one object and the spectrometer device by using at least one distance detector;
  determining at least one material information of the object by evaluating of at least one image of the object determined by at least one pixelated imaging detector by using at least one evaluation device;
  performing at least one spectroscopic analysis of the determined intensities of constituent wavelength signals considering the determined distance information and the material information.

For details, options and definitions, reference may be made to the spectrometer device as discussed above. Thus, specifically, as outlined above, the method may comprise using the spectrometer device according to the present invention, such as according to one or more of the embodiments given above or given in further detail below.

In a further aspect of the present invention, use of the spectrometer device according to the present invention, such as according to one or more of the embodiments given above or given in further detail below, is proposed, for a purpose of use, selected from the group consisting of: a spectroscopy application; an exhaust gas monitoring application; a combustion process monitoring application; a pollution monitoring application; an industrial process monitoring application; a chemical process monitoring application; a food processing process monitoring application; a water quality monitoring application; an air quality monitoring application; a quality control application; a temperature control application; a motion control application; an exhaust control application; a gas sensing application; a gas analytics application; a motion sensing application; a chemical sensing application; a mobile application; a medical application; a mobile spectroscopy application; a food analysis application; an agricultural application such as characterization of soil, silage, feed, crop or produce, monitoring plant health; a plastics identification and/or recycling application.

Overall, in the context of the present invention, the following embodiments are regarded as preferred:

Embodiment 1: A spectrometer device configured for determining at least one spectral or spectroscopic information of at least one object, wherein the spectrometer device is configured for determining intensities of constituent wavelength signals of at least one light beam propagating from the object to the spectrometer device, wherein the spectrometer device comprises at least one distance detector, wherein the distance detector is configured for determining at least one distance information about a distance between the at least one object and the spectrometer device, wherein the spectrometer device comprises at least one pixelated imaging detector configured for determining at least one image of the object, wherein the spectrometer device comprises at least one evaluation device, wherein the evaluation device is configured for determining at least one material information of the object by evaluating of at least one image of the object determined by the pixelated imaging detector, wherein the evaluation device is configured for performing at least one spectroscopic analysis of the determined intensities of constituent wavelength signals considering the determined distance information and the material information.

Embodiment 2: The spectrometer device according to the preceding embodiment, wherein the spectrometer device is a mobile spectrometer device.

Embodiment 3: The spectrometer device according to any one of the preceding embodiments, wherein the spectrometer device comprises at least one wavelength selective element configured for separating incident light into a spectrum of constituent wavelength signals, wherein respective intensities of the constituent wavelength signals are determined by employing at least one pixelated optical detector comprising a plurality of pixels and/or at least one single pixel optical detector.

Embodiment 4: The spectrometer device according to any one of the preceding embodiments, wherein the spectrometer device is configured for contactless spectroscopy.

Embodiment 5: The spectrometer device according to any one of the preceding embodiments, wherein the spectrometer device is configured such that a distance between the object and the spectrometer device is variable.

Embodiment 6: The spectrometer device according to the preceding embodiment, wherein the evaluation device is configured for determining alteration of the distance between the object and the spectrometer device.

Embodiment 7: The spectrometer device according to any one of the two preceding embodiments, wherein the evaluation device is adapted to determine light attenuation due to distance between the object and the spectrometer device from the determined distance information.

Embodiment 8: The spectrometer device according to any one of the preceding embodiments, wherein the spectroscopic analysis comprises determining at least one difference in at least one light property due to presence of the object, wherein the difference in the light property is selected from the group consisting of: at least one wavelength dependent intensity difference; at least one wavelength dependent polarization difference.

Embodiment 9: The spectrometer device according to the preceding embodiment, wherein the distance information is obtained by using one or more of the following techniques: depth-from-photon-ratio, structured light, beam profile analysis, time-of-flight, shape-from-motion, depth-from-focus, triangulation, depth-from-defocus, stereo sensors.

Embodiment 10: The spectrometer device according to any one of the preceding embodiments, wherein the distance detector comprises at least one sensor element having a matrix of optical sensors, the optical sensors each having a light-sensitive area, wherein each optical sensor is configured for generating at least one sensor signal in response to an illumination of the light-sensitive area by at least one light beam propagating from the at least one object to the spectrometer device, wherein at least one first optical sensor of the optical sensors is adapted to generate a first sensor signal in response to illumination by a first constituent wavelength and wherein at least one second optical sensor of the optical sensors is adapted to generate a second sensor signal in response to an illumination by the first constituent wavelength, wherein the evaluation device is configured for determining at least one longitudinal coordinate z of the object by evaluating a combined signal Q from the first sensor signal and the second sensor signal.

Embodiment 11: The spectrometer device according to the preceding embodiment, wherein the combined signal Q is derived by one or more of: forming a quotient of the first signal and the second signal or vice versa; forming a quotient of a multiple of the first signal and a multiple of the second signal or vice versa; forming a quotient of a linear combination of the first signal and a linear combination of the second signal or vice versa; forming a quotient of a first linear combination of the first signal and the second signal and a second linear combination of the first signal and the second signal.

Embodiment 12: The spectrometer device according to any one of the two preceding embodiments, wherein the evaluation device is configured for using at least one predetermined relationship between the combined signal Q and the longitudinal coordinate z of the object for determining the longitudinal coordinate z.

Embodiment 13: The spectrometer device according to any one of the three preceding embodiments, wherein the evaluation device is configured for determining the at least one optical sensor illuminated by the first constituent wavelength and having the highest sensor signal and forming the first sensor signal, wherein the first sensor signal is at least one center signal, wherein the evaluation device is configured for evaluating the sensor signals of the optical sensors of the matrix illuminated by the first wavelength constituent and forming the second sensor signal, wherein the second sensor signal is at least one sum signal, wherein the evaluation device is configured for determining the combined signal Q by combining the center signal and the sum signal Embodiment 14: The spectrometer device according to the preceding embodiment, wherein the center signal is selected from the group consisting of: the highest sensor signal; an average of a group of sensor signals being within a predetermined range of tolerance from the highest sensor signal; an average of sensor signals from a group of optical sensors containing the optical sensor having the highest sensor signal and a predetermined group of neighboring optical sensors; a sum of sensor signals from a group of optical sensors containing the optical sensor having the highest sensor signal and a predetermined group of neighboring optical sensors; a sum of a group of sensor signals being within a predetermined range of tolerance from the highest sensor signal; an average of a group of sensor signals being above a predetermined threshold; a sum of a group of sensor signals being above a predetermined threshold; an integral of sensor signals from a group of optical sensors containing the optical sensor having the highest sensor signal and a predetermined group of neighboring optical sensors; an integral of a group of sensor signals being within a predetermined range of tolerance from the highest sensor signal; an integral of a group of sensor signals being above a predetermined threshold, wherein the sum signal is selected from the group consisting of: an average over all sensor signals of the matrix; a sum of all sensor signals of the matrix; an integral of all sensor signals of the matrix an average over all sensor signals of the matrix except for sensor signals from those optical sensors contributing to the center signal; a sum of all sensor signals of the matrix except for sensor signals from those optical sensors contributing to the center signal; an integral of all sensor signals of the matrix except for sensor signals from those optical sensors contributing to the center signal; a sum of sensor signals of optical sensors within a predetermined range from the optical sensor having the highest sensor signal; an integral of sensor signals of optical sensors within a predetermined range from the optical sensor having the highest sensor signal; a sum of sensor signals above a certain threshold of optical sensors being located within a predetermined range from the optical sensor having the highest sensor signal; an integral of sensor signals above a certain threshold of optical sensors being located within a predetermined range from the optical sensor having the highest sensor signal.

Embodiment 15: The spectrometer device according to any one of the five preceding embodiments, wherein the spectrometer device is adapted to determine at least one further longitudinal coordinate of the object by evaluating the combined signal Q from a first sensor signal and a second sensor signal generated in response to a second constituent wavelength, wherein the evaluation device is adapted to determine a combined longitudinal coordinate from the longitudinal coordinate and the further longitudinal coordinate and to perform the spectroscopic analysis considering the combined longitudinal coordinate.

Embodiment 16: The spectrometer device according to any one of the preceding embodiments, wherein the at least one material information is at least one property selected from the group consisting of: a scattering coefficient, a translucency, a transparency, a deviation from a Lambertian surface reflection, a speckle, material and/or material class; object type and/or object class, and the like.

Embodiment 17: The spectrometer device according to any one of the preceding embodiments, wherein the evaluation device is configured for determining the material information by applying at least one material dependent image filter $\Phi$ to the image of the object determined by the pixelated imaging detector, wherein the material dependent image filter is at least one filter selected from the group consisting of: a luminance filter; a spot shape filter; a squared norm gradient; a standard deviation; a smoothness filter such as a Gaussian filter or median filter; a grey-level-occurrence-based contrast filter; a grey-level-occurrence-based energy filter; a grey-level-occurrence-based homogeneity filter; a grey-level-occurrence-based dissimilarity filter; a Law's energy filter; a threshold area filter; or a linear combination thereof; or a further material dependent image filter $\Phi_{other}$ which correlates to one or more of the luminance filter, the spot shape filter, the squared norm gradient, the standard deviation, the smoothness filter, the grey-leveloccurrence-based energy filter, the grey-level-occurrence-based homogeneity filter, the grey-level-occurrence-based dissimilarity filter, the Law's energy filter, or the threshold area filter, or a linear combination thereof by $|\rho_{\Phi_{other},\Phi_m}| \geq 0.40$ with $\Phi_m$ being one of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof.

Embodiment 18: The spectrometer device according to the preceding embodiment, wherein the material dependent image filter is at least one filter that passes a hypothesis testing, wherein the hypothesis testing uses a Null-hypothesis that the filter does not distinguish between material classifiers and an alternative hypothesis that the filter distinguishes at least two material classifiers, wherein the filter passes the hypothesis testing if a p-value, p, is smaller or equal than a pre-defined level of significance, wherein $p \leq 0.075$, preferably $p \leq 0.05$, more preferably $p \leq 0.025$, most preferably $p \leq 0.01$.

Embodiment 19: The spectrometer device according to any one of the preceding embodiments, wherein the evaluation device is configured for determining the material information by one or more of: comparative image analysis such as based on comparison of the image of the object to an object library; material property analysis such as by comparison of parameters determined from the image of the object to a database with stored parameters such as color, translucency, state of matter or the like.

Embodiment 20: The spectrometer device according to any one of the preceding embodiments, wherein the spectrometer device comprises at least one display device configured for displaying the material information.

Embodiment 21: The spectrometer device according to any one of the preceding embodiments, wherein the spectrometer device is configured for selecting at least one analyte of interest depending on the material information, wherein the spectrometer device is configured to perform at least one spectroscopic analysis for the selected analyte of interest.

Embodiment 22: The spectrometer device according to any one of the preceding embodiments, wherein the spectrometer device comprises at least one illumination source, wherein the illumination source is adapted to illuminate the object with at least one illumination light beam.

Embodiment 23: The spectrometer device according to any one of the preceding embodiments, wherein the illumination source comprises at least one laser source.

Embodiment 24: The spectrometer device according to any one of the preceding embodiments, wherein the pixelated imaging detector is at least one detector selected from the group consisting of: at least one CCD detector; at least one CMOS detector; at least one InGaAs detector.

Embodiment 25: A method for determining at least one difference in at least one light property of at least one light beam originating from at least one object, wherein in the method a spectrometer device according to any one of the preceding embodiments referring to a spectrometer device is used, the method comprising the following steps:
determining intensities of constituent wavelength signals of at least one light beam propagating from the object to the spectrometer device;
determining at least one distance information between at least one object and the spectrometer device by using at least one distance detector;
determining at least one material information of the object by evaluating of at least one image of the object determined by at least one pixelated imaging detector by using at least one evaluation device;
performing at least one spectroscopic analysis of the determined intensities of constituent wavelength signals considering the determined distance information and the material information.

Embodiment 26: The use of a spectrometer device according to any one of the preceding embodiments referring to a spectrometer device for a purpose of use, selected from the group consisting of: an infrared detection application; a spectroscopy application; an exhaust gas monitoring application; a combustion process monitoring application; a pollution monitoring application; an industrial process monitoring application; a chemical process monitoring application; a food processing process monitoring application; a water quality monitoring application; an air quality monitoring application; a quality control application; a temperature control application; a motion control application; an exhaust control application; a gas sensing application; a gas analytics application; a motion sensing application; a chemical sensing application; a mobile application; a medical application; a mobile spectroscopy application; a food analysis application; an agricultural application such as characterization of soil, silage, feed, crop or produce, monitoring plant health; a plastics identification and/or recycling application.

BRIEF DESCRIPTION OF THE FIGURES

Further optional details and features of the invention are evident from the description of preferred exemplary embodiments which follows in conjunction with the dependent claims. In this context, the particular features may be implemented in an isolated fashion or in combination with other features. The invention is not restricted to the exemplary embodiments. The exemplary embodiments are shown schematically in the FIGURES. Identical reference numerals in the individual FIGURES refer to identical elements or elements with identical function, or elements which correspond to one another with regard to their functions.

Specifically, in the FIGURES:

FIG. 1 shows an exemplary embodiment of a spectrometer device according to the present invention.

DETAILED DESCRIPTION OF THE EMBODIMENTS

In FIG. 1, a schematic view of an embodiment of a spectrometer device 110 according to the present invention is depicted. The spectrometer device 110 may be adapted to perform at least one spectroscopic analysis comprising determining at least one difference in at least one light property due to presence of at least one object 112. The difference in the light property may be selected from the group consisting of: at least one wavelength dependent intensity difference; at least one wavelength dependent polarization difference.

The spectrometer device 110 may comprise a wavelength selective element 114 configured for separating incident light into a spectrum of constituent wavelength signals whose respective intensities are determined by employing at least one spectrum detector comprising at least one pixelated optical detector 116. For example, the wavelength selective element 114 may be or may comprise at least one prism. For example, the wavelength selective element 114 may be and/or may comprise at least one optical filter such as a length variable filter.

The pixelated optical detector 116 may comprise at least one sensor element having a matrix of optical sensors 118. The optical sensors 118 each may have a light-sensitive area. Each optical sensor 118 may be configured to generate at least one sensor signal in response to an illumination of the light-sensitive area by at least one light beam propagating from at least one object 112 to the spectrometer device 110. The detector 116 may comprise a series of optical sensors 118 which may, preferably, be arranged in a single line as a one-dimensional matrix along the length of the length variable filter or in more than one line, especially as two, three, or four lines parallel lines, in form of a two-dimensional matrix, in particular, in order to receive most of the intensity of the incident light as possible. Thus, a number N of pixels in one direction may be higher compared to a number M of pixels in a further direction such that the one-dimensional 1×N matrix or a rectangular two-dimensional M×N matrix may be obtained, wherein M<10 and N≥10, preferably N≥20, more preferred N≥50. In addition, the matrixes used herein may also be placed in a staggered arrangement. Herein, each of the optical sensors 118 as used therein may have the same or, within a tolerance level, a similar optical sensitivity, especially for ease of manufacturing the series of the optical sensors 118. However, other kinds of arrangements may also be feasible.

Each of the optical sensors 118 of the pixelated optical detector 116 may be adapted to receive at least a portion of one of the constituent wavelength signals. Each of the constituent wavelength signals is related to an intensity of each constituent wavelength. The light which may pass through the wavelength selective element 114 at a particular spatial position on the wavelength selective element 114 may, subsequently, impinge on the pixelated optical detector 116. In other words, the pixelated optical detector 118 may, preferably, be placed in a manner that the light may first impinge on the wavelength selective element 114 and only that the partition of the light which may pass through the particular spatial position on the wavelength selective element 114 may, thereafter, be capable of impinging on a corresponding spatial position on the pixelated optical detector 116. As a result, the wavelength selective element 114 may, therefore, be used for separating the incident light by its associated wavelength or wavelengths into at least one corresponding spatial position while a particular optical sensor 118 comprised by the pixelated optical detector 116 may, consequently, be employed for measuring an intensity of the incident light which, due to its particular wavelength, may be able to pass through the wavelength selective element 114 at the corresponding spatial position and, therefore, impinge the particular optical sensors 118 provided for determining the intensity of the incident light at the particular wavelength. In a particularly preferred embodiment, the detector 116 may, thus, comprise a sequence of optical sensor 118 which may be located in form of a series of optical sensors 118 one following the other, wherein the sequence of the optical sensors 118 may be placed in a parallel manner with respect to the continuous arrangement of the interference filters along the length of the wavelength selective element 114.

In particular, in order to achieve a high resolution of the spectrometer device, each of the optical sensors 118 may, thus, be adapted to receive incident light only over a small spatial angle. This arrangement, particularly, reflects the setup of the wavelength selective element 114 which is designed to generate the desired spectrum depending on the spatial position of the impingement of the incident light along the length of the wavelength selective element 114. This particular arrangement may be achieved by a pixelated optical detector 116 which comprises a plurality of optical sensors 118, in particular a plurality of pixelated optical sensors 118, wherein each of the optical sensors 118 is adapted to receive at least a portion of one of the constituent wavelength signals as provided by the length variable filter. As indicated above, each of the constituent wavelength signals is, hereby, related to an intensity of each of the constituent wavelengths.

The pixelated optical detector 116 may be designed to generate signals, preferably electronic signals, associated with the intensity of the incident light which impinges on the individual optical sensor 118. The signal may be an analogue and/or a digital signal. The electronic signals for adjacent optical sensors can, accordingly, be generated simultaneously or else in a temporally successive manner. By way of example, during a row scan or line scan, it is possible to generate a sequence of electronic signals which correspond to the series of the individual pixels which are arranged in a line. In addition, the individual optical sensors 118 may, preferably, be active pixel sensors which may be adapted to amplify the electronic signals prior to providing it to the external evaluation unit. For this purpose, the pixelated optical detector 116 may comprise one or more signal processing devices, such as one or more filters and/or analogue-digital-converters for processing and/or preprocessing the electronic signals.

The pixelated optical detector 116 may be selected from any known pixel sensor, in particular, from a pixelated organic camera element, preferably, a pixelated organic camera chip, or from a pixelated inorganic camera element, preferably, a pixelated inorganic camera chip, more preferably from a CCD chip or a CMOS chip, which are, commonly, used in various cameras nowadays. As an alternative, the pixelated optical detector may be or comprise a photoconductor, in particular an inorganic photoconductor, especially PbS, PbSe, Ge, InGaAs, ext. InGaAs, InSb, or HgCdTe. As a further alternative it may comprise of pyroelectric, bolometer or thermopile detector elements. Thus, a camera chip having a matrix of 1×N pixels or of M×N pixels may be used here, wherein M<10 and N≥10, preferably N≥20, more preferred N≥50. Further, a mono-chrome camera element, preferably a monochrome camera chip, may be used, wherein the monochrome camera element may be differently selected for each pixel sensor, especially, in accordance with the varying wavelength along the series of the optical sensors.

As a further alternative, the pixelated optical detector 116 may be based on a FiP sensor which is, among further documents, disclosed in WO 2012/110924 A1, WO 2014/097181 A1, or WO 2016/120392 A1. Alternatively, further kinds of pixelated optical detectors may also be feasible.

Thus, the pixelated optical detector 116 may be adapted to provide a plurality of the electrical signals which may be generated by the photosensitive areas of the optical sensors comprised by the pixelated optical detector. The electrical signals as provided by the pixelated optical detector of the spectrometer device 110 may, subsequently, be forwarded to an evaluation device 120. The evaluation device 120 may be configured for determining information related to the spectrum of the object 112 of which a spectrum has been recorded, in particular, by using the spectrometer device 110 as described herein, wherein the information is obtainable by evaluating the detector signals as provided by the pixelated optical detector 116. The information may, for example, be provided electronically, visually, acoustically or in any arbitrary combination thereof. Further, the information may be stored in a data storage device of the spectrometer device 110 or of a separate storage device and/or may be provided via at least one interface 122, such as a wireless interface and/or a wire-bound interface, for example to at least one external device such as a display device or the like.

The spectrometer device 110 may comprise at least one concentrator device, not shown here, for directing the light beam to the wavelength selective element 114. In addition, the spectrometer device 110 may, further, comprise at least one transfer device 124. A light beam 126 which emerges from the object 112 may travel firstly through the transfer device 124 until it may, subsequently, pass the wavelength selective element 114 until it may, finally, impinge the pixelated optical detector 116. The transfer device 124 may be selected from a group consisting of an optical lens, a curved mirror, a grating, and a diffractive optical element. More particular, the optical lens may, especially, be selected from a group consisting of a biconvex lens, a plano-convex lens, a biconcave lens, a plano-concave lens, an aspherical lens, a cylindrical lens and a meniscus lens. Hereby, the transfer device 124 may comprise a material which may be at least partially transparent, preferably over the whole wavelength range of the wavelength selective element 114 as indicated above. For this purpose, the same or similar optically transparent materials as mentioned in this respect can also be used. However, further optical elements may also be feasible.

The light beam 126 emerging from the object 112 can originate in the object itself, but can also optionally have a different origin and propagate from this origin to the object 112 and subsequently toward the spectrometer device 110. The latter case can, in particular, be affected by at least one illumination source 128 being used. Thus, the light beam 126 propagating from the object 112 to the spectrometer device 110 may be light which may be reflected by the object 112 and/or a reflection device connected to the object 112. Alternatively or in addition, the light may at least partially transmit through the object 112.

The spectrometer device 110 may comprise the illumination source 128. The illumination source 128 can be embodied in various ways. Thus, the illumination source 128 can be for example part of the spectrometer device 110 in a housing 130. Alternatively or additionally, however, the illumination source 128 can also be arranged outside the housing 130, for example as a separate light source. The illumination source 128 can be arranged separately from the object 112 and illuminate the object 112 from a distance. The illumination source 128 may, preferably, comprise a kind of illumination source which may be known to provide sufficient emission in visual spectral range and/or in the infrared (IR) spectral range, especially, in the near infrared (NIR) spectral range, in particular, an incandescent lamp. Alternatively or in addition, the illumination source 128 may, be selected from at least one of the following illumination sources: a laser, in particular a laser diode, although further types of lasers can also be used; a light emitting diode; an organic light source, in particular an organic light emitting diode; a neon light; a structured light source; a flame source; a heat source. Alternatively or additionally, other illumination sources can be used.

The spectrometer device 110 is configured for determining at least one distance information about a distance between at least one object 112 and the spectrometer device 110. The spectrometer device 110 may be adapted for determining the distance information and the information related to the spectrum of the object 112 simultaneously or subsequently. The spectrometer device 110 may be adapted to perform the determination of the distance information, such as the longitudinal coordinate, before and/or during and/or after the spectroscopic measurement. The spectrometer device 110 may constitute a coordinate system, wherein a longitudinal coordinate is a coordinate along an optical axis 132 of the spectrometer device 110. The coordinate system may be a polar coordinate system in which the optical axis 132 of the spectrometer device 110 forms a z-axis and in which a distance from the z-axis and a polar angle may be used as additional coordinates. A direction parallel or antiparallel to the z-axis may be considered a longitudinal direction, and a coordinate along the z-axis may be considered a longitudinal coordinate or distance. Any direction perpendicular to the z-axis may be considered a transversal direction, and the polar coordinate and/or the polar angle may be considered a transversal coordinate. The distance between the object 112 and the spectrometer device 110 may be obtained by using one or more of: depth-from-photon-ratio, structured light, beam profile analysis, time-of-flight, shape-from-motion, depth-from-focus, triangulation, depth-from-defocus, stereo sensors. Furthermore, the distance information may be obtained using at least one FiP sensor as described in WO 2012/110924 A1 or WO 2014/097181 A1.

FIG. 1 shows an embodiment, wherein spectrometer device 110 comprises at least one distance detector 134 configured for determining the distance between the object 112 and the spectrometer device 110. The distance between the object 112 and the spectrometer device 110 may be obtained by using one or more of the following techniques: depth-from-photon-ratio, structured light, beam profile analysis, time-of-flight, shape-from-motion, depth-from-focus, triangulation, depth-from-defocus, stereo sensors. For example, the distance detector 134 may be configured for determining the distance based on triangulation principle, such as at least one triangulation proximity sensor and/or based on the time-of-flight (TOF) principle. The spectrometer device 110 may comprise at least one time-of-flight sensor. The time-of-flight sensor may be adapted to generate at least one sensor signal dependent on a time-of-flight an illumination light beam 136 has traveled, e.g. from the illumination source 128, to the object 112 and the light beam 126 has traveled from the object 112 to time-of flight sensor. The time-of-flight sensor may be selected from the group consisting of: at least one pulsed time-of-flight detector; at least one phase modulated time-of-flight detector; at least one direct time-of-flight detector; at least one indirect time-of-flight detector. For example, the pulsed time-of-flight detector may be at least one range gated imager and/or at least one direct time-of-flight imager. For example the phase modulated time-of-flight detector may be at least one RF-modulated light source with at least one phase detector. The time-of-flight sensor may be adapted to determine a time delay between emission of the illumination light beam by the illumination source and receipt of the reflection light beam.

Specifically, FIG. 1 shows an embodiment in which the spectrometer device 110, in particular the distance detector 134, may be adapted to determine the position based on the depth-from-photon-ratio technique. With respect to details of methods and devices based on the depth-from-photon-ratio technique reference is made to international patent applications number PCT/EP2017/079577, PCT/EP2017/079558, PCT/EP2017/079564 filed on Nov. 17, 2017 and PCT/EP2018/056545 filed on Mar. 15, 2018 the full content of which is included by reference. Depth-from-photon-ratio is a distance measurement technology that is very flexible concerning the detector technology and, thus, also very flexible concerning the wavelength of the employed light source. Known mobile spectrometer technologies use silicon, InAs, InGaAs, or extended InGaAs detectors, wherein silicon is very limited in its wavelength regime and both InAs and InGaAs are expensive. Lead salt detectors show promise for mobile applications due to novel encapsulation technologies allowing compact sensor designs, see e.g. WO 2018/019921 A1. Using depth-from-photon-ratio may allows reliable distance measurement and easy implementation in a spectrometer with little additional effort The distance detector 134 may comprises the at least one sensor element having a matrix of optical sensors. Additionally or alternatively, the pixelated optical detector 116 may be used as sensor element. In each case, the optical sensors each may have a light-sensitive area. Each optical sensor may be configured for generating at least one sensor signal in response to an illumination of the light-sensitive area by at least one light beam propagating from at least one object to the spectrometer device. At least one first optical sensor of the optical sensors may be adapted to generate a first sensor signal in response to illumination by a first constituent wavelength and at least one second optical sensor of the optical sensors may be adapted to generate a second sensor signal in response to an illumination by the first constituent wavelength. The evaluation device 120 may be configured for determining at least one longitudinal coordinate z of the object 112 by evaluating a combined signal Q from the first sensor signal and the second sensor signal. The evaluation device 120 may be configured for evaluating at least one sensor signal generated by the optical sensors of the matrix of optical sensors by performing at least one spectroscopic analysis considering the determined longitudinal coordinate z.

The optical sensors for determining the distance information and the optical sensors used for spectroscopy may be identical, and may be embodied as optical sensors 118. Specifically, the optical sensors for determining the distance information may be used as optical sensors for spectroscopy or the other way round. Thus, the optical sensors for determining the distance information may correspond to or may be designed as the optical sensors for spectroscopy and/or the matrix of optical sensors of the sensor element may correspond to or may be designed as pixelated optical sensor 116.

The optical sensors 118 and/or the optical sensors of the distance detector 134 specifically may be or may comprise at least one photodetector, preferably inorganic photodetectors, more preferably inorganic semiconductor photodetectors, most preferably silicon photodetectors. Specifically, the optical sensors may be sensitive in the infrared spectral range. All pixels of the matrix or at least a group of the optical sensors of the matrix specifically may be identical. Groups of identical pixels of the matrix specifically may be provided for different spectral ranges, or all pixels may be identical in terms of spectral sensitivity. Further, the pixels may be identical in size and/or with regard to their electronic or optoelectronic properties. Specifically, the optical sensors 118 may be or may comprise at least one inorganic photodiode which are sensitive in the infrared spectral range, preferably in the range of 700 nm to 3.0 micrometers. Specifically, the optical sensors 118 may be sensitive in the part of the near infrared region where silicon photodiodes are applicable specifically in the range of 700 nm to 1100 nm. Infrared optical sensors which may be used for optical sensors may be commercially available infrared optical sensors, such as infrared optical sensors commercially available under the brand name Hertzstueck™ from trinamiX GmbH, D-67056 Ludwigshafen am Rhein, Germany. Thus, as an example, the optical sensors 118 may comprise at least one optical sensor of an intrinsic photovoltaic type, more preferably at least one semiconductor photodiode selected from the group consisting of: a Ge photodiode, an InGaAs photodiode, an extended InGaAs photodiode, an InAs photodiode, an InSb photodiode, a HgCdTe photodiode. Additionally or alternatively, the optical sensors may comprise at least one optical sensor of an extrinsic photovoltaic type, more preferably at least one semiconductor photodiode selected from the group consisting of: a Ge:Au photodiode, a Ge:Hg photodiode, a Ge:Cu photodiode, a Ge:Zn photodiode, a Si:Ga photodiode, a Si:As photodiode. Additionally or alternatively, the optical sensors may comprise at least one photoconductive sensor such as a PbS or PbSe sensor, a bolometer, preferably a bolometer selected from the group consisting of a VO bolometer and an amorphous Si bolometer.

For determining a longitudinal coordinate of the object 112 using depth-from-photon-ratio technology at least two optical sensors may be employed. For obtaining the distance information the distance detector 134 may comprise at least one optical sensor and/or a plurality of optical sensors. Specifically, for spectroscopy, one optical sensor 118 in combination with a prism or several optical sensors in combination with an optical filer may be employed. For example, one of the optical sensors 118 used for determining a longitudinal coordinate of the object using depth-from-photon-ratio technology may be employed for spectroscopy. For example, the pixelated optical detector 116 may be configured for spectroscopy and for determining the longitudinal coordinate of the object 112 using depth-from-photon-ratio technology. Thus, using depth-from-photon-ratio may allow reliable distance measurement and easy implementation in a spectrometer with little additional effort.

Each optical sensor of the distance detector 134 and/or each optical sensor 118 of the matrix of optical sensors 118 may be configured to generate at least one sensor signal in response to an illumination of the light-sensitive area by at least one light beam, in particular having one constituent wavelength, propagating from at least one object 112 to the spectrometer device 110. At least one first optical sensor of the distance detector 134 and/or of the optical sensors 118 may be adapted to generate a first sensor signal in response to illumination by a first constituent wavelength and at least one second optical sensor of the distance detector 134 and/or of the optical sensors 118 may be adapted to generate a second sensor signal in response to an illumination by the first constituent wavelength.

The evaluation device 120 may be adapted to evaluate the combined signal. Thereby, the at least one longitudinal coordinate of the object 112 is determined. The evaluating may comprises evaluating the combined signal from the first sensor signal and the second sensor signal. The evaluation device 120 may be configured for deriving the combined signal by one or more of dividing the sensor signals, dividing multiples of the sensor signals, dividing linear combinations of the sensor signals. The evaluation device 120 may be configured for using at least one predetermined relationship between the combined signal and the longitudinal coordinate for determining the longitudinal coordinate. The predetermined relationship may be one or more of an empiric relationship, a semi-empiric relationship and an analytically derived relationship. The evaluation device 120 may comprise at least one data storage device for storing the predetermined relationship, such as a lookup list or a lookup table.

The combined signal may be determined by using various means. As an example, a software means for deriving a quotient signal, a hardware means for deriving the quotient signal, or both, may be used and may be implemented in the evaluation device 120. Thus, the evaluation device 120, as an example, may comprise at least one divider 138, wherein the divider 138 is configured for deriving the quotient signal. The divider 138 may fully or partially be embodied as one or both of a software divider or a hardware divider. The divider 138 may fully or partially be integrated into the sensor element answers or may fully or partially be embodied independent from the sensor element.

For example, the combined signal Q, are derived by $$Q(z_o) = \frac{\iint_{A_1} E(x, y, z_o) dx dy}{\iint_{A_2} E(x, y, z_o) dx dy}$$

wherein x and y are transversal coordinates, A1 and A2 are different areas of the at least one beam profile at the position of the sensor element of the distance detector 134, and $E(x,y,z_o)$ denotes a beam profile given at the distance $z_o$. The beam profile may be selected from the group consisting of a trapezoid beam profile; a triangle beam profile; a conical beam profile and a linear combination of Gaussian beam profiles. Area A1 and area A2 may differ. In particular, A1 and A2 are not congruent. Thus, A1 and A2 may differ in one or more of the shape or content. Each of the sensor signals may comprises at least one information of at least one area of the beam profile. Generally the beam profile is dependent on luminance $L(z_o)$ and beam shape $S(x,y;z_o)$, $E(x,y;z_o)$ =L·S. Thus, by deriving the combined signal it may allow determining the longitudinal coordinate independent from luminance. In addition, using the combined signal allows determination of the distance $z_o$ independent from an object size. Thus, the combined signal allows determination of the distance $z_o$ independent from the material properties and/or reflective properties and/or scattering properties of the object 112 to be measured and independent from alterations of the light source such as by manufacturing precision, heat, water, dirt, damages on the lens, or the like.

Each of the first sensor signal and the second sensor signal may comprise at least one information of the at least one area of the beam profile. The light-sensitive areas may be arranged such that one of the sensor signals comprises information of a first area of the beam profile and the other one of the sensor signals comprises information of a second area of the beam profile. The first area of the beam profile and the second area of the beam profile may be one or both of adjacent or overlapping regions. The first area and the second area may be not congruent in area. The first area of the beam profile may comprise essentially edge information of the beam profile and the second area of the beam profile may comprise essentially center information of the beam profile. The edge information may comprise information relating to a number of photons in the first area of the beam profile and the center information comprises information relating to a number of photons in the second area of the beam profile. The evaluation device 120 may be configured to determine and/or to select the first area of the beam profile and the second area of the beam profile. The beam profile may have a center, i.e. a maximum value of the beam profile and/or a center point of a plateau of the beam profile and/or a geometrical center of the light spot, and falling edges extending from the center. The second region may comprise inner regions of the cross section and the first region may comprise outer regions of the cross section. Preferably the center information has a proportion of edge information of less than 10%, more preferably of less than 5%, most preferably the center information comprises no edge content. The edge information may comprise information of the whole beam profile, in particular from center and edge regions. The edge information may have a proportion of center information of less than 10%, preferably of less than 5%, more preferably the edge information comprises no center content. At least one area of the beam profile may be determined and/or selected as second area of the beam profile if it is close or around the center and comprises essentially center information. At least one area of the beam profile may be determined and/or selected as first area of the beam profile if it comprises at least parts of the falling edges of the cross section. For example, the whole area of the cross section may be determined as first region. The first area of the beam profile may be area A1 and the second area of the beam profile may be area A2.

Other selections of the first area A1 and second area A2 may be feasible. For example, the first area may comprise essentially outer regions of the beam profile and the second area may comprise essentially inner regions of the beam profile. For example, in case of a two-dimensional beam profile, the beam profile may be divided in a left part and a right part, wherein the first area may comprise essentially areas of the left part of the beam profile and the second area may comprise essentially areas of the right part of the beam profile.

The edge information may comprise information relating to a number of photons in the first area of the beam profile and the center information may comprise information relating to a number of photons in the second area of the beam profile. The evaluation device 120 may be adapted for determining an area integral of the beam profile. The evaluation device 120 may be adapted to determine the edge information by integrating and/or summing of the first area. The evaluation device may be adapted to determine the center information by integrating and/or summing of the second area. For example, the beam profile may be a trapezoid beam profile and the evaluation device may be adapted to determine an integral of the trapezoid. Further, when trapezoid beam profiles may be assumed, the determination of edge and center signals may be replaced by equivalent evaluations making use of properties of the trapezoid beam profile such as determination of the slope and position of the edges and of the height of the central plateau and deriving edge and center signals by geometric considerations. Additionally or alternatively, the evaluation device 120 may be adapted to determine one or both of center information or edge information from at least one slice or cut of the light spot. This may be realized, for example, by replacing the area integrals in the combined signal by a line integral along the slice or cut. For improved accuracy, several slices or cuts through the light spot may be used and averaged. In case of an elliptical spot profile, averaging over several slices or cuts may result in improved distance information.

As explained, e.g. in WO 2012/110924 A1 or WO 2014/097181 A1, typically, a predetermined or determinable relationship exists between a size of a light spot, such as a diameter of the light spot, a beam waist or an equivalent diameter, and the longitudinal coordinate of the object from which the light beam propagates towards the sensor element. Without wishing to be bound by this theory, the light spot may be characterized by two measurement variables: a measurement signal measured in a small measurement patch in the center or close to the center of the light spot, also referred to as the center signal, and an integral or sum signal integrated over the light spot, with or without the center signal. For a light beam having a certain total power which does not change when the beam is widened or focused, the sum signal should be independent from the spot size of the light spot, and, thus, should, at least when linear optical sensors within their respective measurement range are used, be independent from the distance between the object 112 and the spectrometer device 110. The center signal, however, is dependent on the spot size. Thus, the center signal typically increases when the light beam is focused, and decreases when the light beam is defocused. By comparing the center signal and the sum signal, thus, an item of information on the size of the light spot generated by the light beam and, thus, on the longitudinal coordinate of the location of reflection may be generated. The comparing of the center signal and the sum signal, as an example, may be done by forming the combined signal Q out of the center signal and the sum signal and by using a predetermined or determinable relationship between the longitudinal coordinate and the combined signal for deriving the longitudinal coordinate.

The evaluation device 120 may be adapted to determine those optical sensors of the distance detector 134 and/or of the optical sensors 118 illuminated by the first wavelength constituent. The evaluation device 120 may be configured for determining the at least one optical sensor 118 illuminated by the first constituent wavelength and having the highest sensor signal and forming the first sensor signal. The first sensor signal may be at least one center signal. The evaluation device 120 may be configured for evaluating the sensor signals of the optical sensors of the distance detector 134 and/or of the optical sensors 118 illuminated by the first wavelength constituent and forming the second sensor signal. The second sensor signal is at least one sum signal. The evaluation device 120 may be configured for determining the combined signal Q by combining the center signal and the sum signal.

For example, the center signal may be the signal of the at least one optical sensor of the distance detector 134 and/or of the optical sensors 118 and/or pixel having the highest sensor signal out of the plurality of sensor signals generated by the optical sensors of the distance detector 134 and/or of the optical sensors 118 and/or pixels of the entire matrix or of a region of interest within the matrix, wherein the region of interest may be predetermined or determinable within an image generated by the optical sensors 118 and/or pixels of the matrix. The center signal may arise from a single optical sensor of the distance detector 134 and/or of the optical sensors 118 and/or pixel or from a group of optical sensors of the distance detector 134 and/or of the optical sensors 118, wherein, in the latter case, as an example, the sensor signals of the group of optical sensors and/or pixels may be added up, integrated or averaged, in order to determine the center signal. The group of optical sensors of the distance detector 134 and/or of the optical sensors 118 and/or pixels from which the center signal arises may be a group of neighboring optical sensors and/or pixels, such as optical sensors and/or pixels having less than a predetermined distance from the actual optical sensor and/or pixel having the highest sensor signal, or may be a group of optical sensors and/or pixels generating sensor signals being within a predetermined range from the highest sensor signal. The group of optical sensors of the distance detector 134 and/or of the optical sensors 118 and/or pixels from which the center signal arises may be chosen as large as possible in order to allow maximum dynamic range. The evaluation device 120 may be adapted to determine the center signal by integration of the plurality of sensor signals, for example the plurality of optical sensors and/or pixels around the optical sensor 118 and/or pixel having the highest sensor signal.

As outlined above, the center signal generally may be a single sensor signal, such as a sensor signal from the optical sensor and/or pixel in the center of the light spot, or may be a combination of a plurality of sensor signals, such as a combination of sensor signals arising from optical sensors and/or pixels in the center of the light spot, or a secondary sensor signal derived by processing a sensor signal derived by one or more of the aforementioned possibilities. The determination of the center signal may be performed electronically, since a comparison of sensor signals is fairly simply implemented by conventional electronics, or may be performed fully or partially by software. Specifically, the center signal may be selected from the group consisting of: the highest sensor signal; an average of a group of sensor signals being within a predetermined range of tolerance from the highest sensor signal; an average of sensor signals from a group of optical sensors and/or pixels containing the optical sensor and/or pixel having the highest sensor signal and a predetermined group of neighboring optical sensors and/or pixels; a sum of sensor signals from a group of optical sensors and/or pixels containing the optical sensor and/or pixel having the highest sensor signal and a predetermined group of neighboring optical sensors and/or pixels; a sum of a group of sensor signals being within a predetermined range of tolerance from the highest sensor signal; an average of a group of sensor signals being above a predetermined threshold; a sum of a group of sensor signals being above a predetermined threshold; an integral of sensor signals from a group of optical sensors containing the optical sensor having the highest sensor signal and a predetermined group of neighboring optical sensors; an integral of a group of sensor signals being within a predetermined range of tolerance from the highest sensor signal; an integral of a group of sensor signals being above a predetermined threshold.

For example, the sum signal may be derived by adding up the sensor signals, integrating over the sensor signals or averaging over the sensor signals of the entire matrix or of a region of interest within the matrix, wherein the region of interest may be predetermined or determinable within an image generated by the optical sensors of the distance detector 134 and/or of the optical sensors 118 of the matrix. When adding up, integrating over or averaging over the sensor signals, the actual optical sensors from which the sensor signal is generated may be left out of the adding, integration or averaging or, alternatively, may be included into the adding, integration or averaging. The evaluation device 120 may be adapted to determine the sum signal by integrating signals of the entire matrix, or of the region of interest within the matrix. For example, the beam profile may be a trapezoid beam profile and the evaluation device may be adapted to determine an integral of the entire trapezoid. Further, when trapezoid beam profiles may be assumed, the determination of edge and center signals may be replaced by equivalent evaluations making use of properties of the trapezoid beam profile such as determination of the slope and position of the edges and of the height of the central plateau and deriving edge and center signals by geometric considerations.

Similarly, the center signal and edge signal may also be determined by using segments of the beam profile such as circular segments of the beam profile. For example, the beam profile may be divided into two segments by a secant or a chord that does not pass the center of the beam profile. Thus, one segment will essentially contain edge information, while the other segment will contain essentially center information. For example, to further reduce the amount of edge information in the center signal, the edge signal may further be subtracted from the center signal.

The combined signal Q may be a signal which is generated by combining the center signal and the sum signal. Specifically, the determining may include one or more of: forming a quotient of the center signal and the sum signal or vice versa; forming a quotient of a multiple of the center signal and a multiple of the sum signal or vice versa; forming a quotient of a linear combination of the center signal and a linear combination of the sum signal or vice versa. Additionally or alternatively, the combined signal Q may comprise an arbitrary signal or signal combination which contains at least one item of information on a comparison between the center signal and the sum signal.

The spectrometer device 110 may be configured for determining at least one spectral or spectroscopic information of the at least one object 112. The spectrometer device 110 comprises the at least one evaluation device 120 configured for performing at least one spectroscopic analysis considering the determined distance information. The evaluation device 120 may be configured for performing at least one spectroscopic analysis considering the determined longitudinal coordinate z. In the spectroscopic analysis at least one spectral or spectroscopic information of the object may be determined. Specifically, the evaluation device 120 may be configured for determining light attenuation due to the distance between the object and the spectrometer device 110. The spectroscopic analysis may comprise determining at least one difference in at least one light property due to presence of the object 112. The difference in the light property may be selected from the group consisting of: at least one wavelength dependent intensity difference; at least one wavelength dependent polarization difference. The evaluation device 120 may be adapted to perform the spectroscopic analysis considering the light attenuation. The evaluation device 120 may be adapted to correct intensities of the spectrum of constituent wavelength signals determined by the optical detector. Specifically, the evaluation device 120 may be adapted to correct the determined intensity values for light attenuation, for example by multiplying and/or dividing the determined intensity values with at least one correction function. The correction function may be determined empirically and/or semi-empirically and/or analytically. For example, the spectrometer device may be configured for determining light attenuation by measuring a background spectrum depending on optics, light source, characteristics of light sources, dirt and the like. The spectrometer device 110 may be configured for deriving the correction function, such as a background correction function, therefrom. However, during measuring of the background spectrum the distance between object and spectrometer may be kept fixed. The spectrometer device may be a mobile spectrometer device. Specifically, the distance between the object 112 and the spectrometer device 110 may be variable. The evaluation device 120 may be configured for determining alteration of the distance between the object 112 and the spectrometer device 110. Thus, the intensity values and/or the background spectrum have to be corrected further for influences due to distance and alteration in distance between object and spectrometer device. The evaluation device 120 may be adapted to correct the determined light attenuation for influences due to the distance between the object and the spectrometer. For correction of light attenuation due to distance a further correction function such as a polynomial correction function, for example a second order or higher order polynomial, may be used. For example, the distance dependent light attenuation may be corrected by a fraction of polynomials in z such as a polynomial up to third order in z divided by a polynomial up to fifth order in z, whereas coefficients may be used to adjust the distance dependent light attenuation function. For example, the correction function may be a rational polynomial function. For example, a polynomial $A \cdot 1/z^2$, with A being a coefficient or constant and z being the longitudinal coordinate z, may be used. The further correction function may be determined considering light emitting characteristics of the illumination source. In addition, the further correction function may be determined by considering per-determined reflection properties of the object, e.g. determined using spot profiles, and/or assumed reflection properties of the object. Further, the correction function may be a combined correction function correcting the light attenuation due to optics, ambient light, dirt, temperature, and correcting the distance dependent light attenuation simultaneously.

As an example, the combined correction function may be a product of a distance independent correction function such as a background correction function and a distance dependent correction function.

The spectrometer device 110 may be adapted to determine at least one further longitudinal coordinate of the object by evaluating the combined signal Q from a first sensor signal and a second sensor signal generated in response to a second constituent wavelength. The evaluation device 120 may be adapted to determine a combined longitudinal coordinate, such as a mean value, from the longitudinal coordinate and the further longitudinal coordinate and to perform the spectroscopic analysis considering the combined longitudinal coordinate.

The spectrometer device 110 may be configured for contactless spectroscopy. Determining the distance information and using the distance information for correction of the spectroscopic measurement allows for variable distances between the object and the spectrometer device. Direct mechanical contact or use of special sample boxes can be avoided.

The evaluation device 120 is configured for determining material information of the object 112 by evaluating of at least one image of the object 112 determined by at least one imaging detector 121, wherein in FIG. 1 one or both of the pixelated optical detector 116 or the distance detector 134 may be used as imaging detector 121. For example, the material information may be at least one property selected from the group consisting of: a scattering coefficient, a translucency, a transparency, a deviation from a Lambertian surface reflection, a speckle, material and/or material class; object type and/or object class, and the like. The material information may comprise information about a material property. For example, the material property may be a property selected from the group consisting of: roughness, penetration depth of light into the material, a property characterizing the material as biological or non-biological material, a reflectivity, a specular reflectivity, a diffuse reflectivity, a surface property, a measure for translucence, a scattering, specifically a back-scattering behavior or the like. The at least one material property may be a property selected from the group consisting of: a scattering coefficient, a translucency, a transparency, a deviation from a Lambertian surface reflection, a speckle, and the like.

The evaluation device 120 may comprise at least one database 140 comprising a list and/or table, such as a lookup list or a lookup table, of predefined and/or predetermined material information. The list and/or table of material information may be determined and/or generated by performing at least one test measurement using the spectrometer according to the present invention, for example by performing material tests using samples having known material properties. The list and/or table of material information may be determined and/or generated at the manufacturer site and/or by the user of the spectrometer device. The material information may additionally be assigned to a material classifier such as one or more of a material name, a material group such as biological or non-biological material, translucent or non-translucent materials, metal or non-metal, skin or non-skin, fur or non-fur, carpet or non-carpet, reflective or non-reflective, specular reflective or non-specular reflective, foam or non-foam, hair or non-hair, roughness groups or the like. The evaluation device 120 may comprise the at least one database 142 comprising a list and/or table comprising the material information and associated material name and/or material group.

The object 112 may comprise one or more articles and/or one or more parts of an article, wherein the at least one article or the at least one part thereof may comprise at least one component which may provide a spectrum suitable for investigations. Additionally or alternatively, the object 112 may be or may comprise one or more living beings and/or one or more parts thereof, such as one or more body parts or bodily fluids of a human being, e.g. a user, or of an animal. For example, the object 112 may be at least one object selected from the group consisting of: a scene, a human such as a human, wood, carpet, foam, an animal such as a cow, a plant, a piece of tissue, a metal, a toy, a metallic object, a beverage, a food such as a fruit, meat, fish, a dish, a cosmetics product, an applied cosmetics product, cloth, fur, hair, a maintenance product, a cream, an oil, a powder, a carpet, a juice, a suspension, a paint, a plant, a body, a part of a body, organic material, inorganic material, a reflective material, a screen, a display, a wall, a sheet of paper, such as a photograph. The object 112 may comprise at least one surface on which the illumination is projected. The surface may be adapted to at least partially reflect the illumination towards the spectrometer device. For example, without wishing to be bound by this theory, human skin may have a reflection profile, also denoted back scattering profile, comprising parts generated by back reflection of the surface, denoted as surface reflection, and parts generated by very diffuse reflection from light penetrating the skin, denoted as diffuse part of the back reflection. With respect to reflection profile of human skin reference is made to "Lasertechnik in der Medizin: Grundlagen, Systeme, Anwendungen", "Wirkung von Laserstrahlung auf Gewebe", 1991, pages 171 to 266, Jürgen Eichler, Theo Seiler, Springer Verlag, ISBN 0939-0979. The surface reflection of the skin may increase with the wavelength increasing towards the near infrared. Further, the penetration depth may increase with increasing wavelength from visible to near infrared. The diffuse part of the back reflection may increase with penetrating depth of the light. These material properties may be used to distinguish skin from other materials, specifically by analyzing the back scattering profile.

Specifically, the spectrometer device 110 may be configured for detection of biological tissue, in particular human skin. The spectrometer device 110 may be a device for detection, in particular optical detection, of biological tissue, in particular of human skin. The detection of biological tissue may comprise determining and/or validating whether a surface to be examined or under test is or comprises biological tissue, in particular human skin, and/or to distinguish biological tissue, in particular human skin, from other tissues, in particular other surfaces, and/or distinguishing different types of biological tissue such as distinguishing different types of human tissue e.g. muscle, fat, organs, or the like. For example, the biological tissue may be or may comprise human tissue or parts thereof such as skin, hair, muscle, fat, organs, or the like. For example, the biological tissue may be or may comprise animal tissue or a part thereof such as skin, fur, muscle, fat, organs, or the like. For example, the biological tissue may be or may comprise plant tissue or a part thereof. The spectrometer device 110 may be adapted to distinguish animal tissue or parts thereof from one or more of inorganic tissue, metal surfaces, plastics surfaces, for example of farming machines or milking machines. The spectrometer device 110 may be adapted to distinguish plant tissue or parts thereof from one or more of inorganic tissue, metal surfaces, plastics surfaces, for example of farming machines. The spectrometer device 110 may be adapted to distinguish food and/or beverage from dish and/or glasses. The spectrometer device 110 may be adapted to distinguish different types of food such as a fruit, meat, and fish. The spectrometer device 110 may be adapted to distinguish a cosmetics product and/or, an applied cosmetics product from human skin. The spectrometer device 110 may be adapted to distinguish human skin from foam, paper, wood, a display, a screen. The spectrometer device may be adapted to distinguish human skin from cloth. The spectrometer device 110 may be adapted to distinguish a maintenance product from material of machine components such metal components etc. The spectrometer device 110 may be adapted to distinguish organic material from inorganic material. The spectrometer device 110 may be adapted to distinguish human biological tissue from surfaces of artificial or non-living objects. The spectrometer device 110 may be used, in particular, for non-therapeutic and non-diagnostic applications.

The evaluation device 120 may be configured for determining the material information by applying at least one material dependent image filter $\Phi$ to the image of the object 112 determined by the imaging detector 121. Specifically, the evaluation device 120 may be configured for determining at least one material feature $\varphi_m$ by applying the material dependent image filter $\Phi$ to the image of the object 112 determined by the pixelated optical detector 116 and/or the distance detector 134.

The material dependent image filter may be at least one filter selected from the group consisting of: a luminance filter; a spot shape filter; a squared norm gradient; a standard deviation; a smoothness filter such as a Gaussian filter or median filter; a grey-level-occurrence-based contrast filter; a grey-level-occurrence-based energy filter; a grey-level-occurrence-based homogeneity filter; a grey-level-occurrence-based dissimilarity filter; a Law's energy filter; a threshold area filter; or a linear combination thereof; or a further material dependent image filter $\Phi_{other}$ which correlates to one or more of the luminance filter, the spot shape filter, the squared norm gradient, the standard deviation, the smoothness filter, the grey-level-occurrence-based energy filter, the grey-level-occurrence-based homogeneity filter, the greylevel-occurrence-based dissimilarity filter, the Law's energy filter, or the threshold area filter, or a linear combination thereof by $|\rho_{\Phi_{other},\Phi_m}| \geq 0.40$ with $\Phi_m$ being one of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof.

The pixelated optical detector 116 may be configured for recording a beam profile of at least one reflection feature of the image of the object 112. The evaluation device 120 may be configured for identifying and/or selecting the at least one reflection feature in the image, specifically at least one light spot, provided by the pixelated optical detector 116. The evaluation device 120 may be configured for performing at least one image analysis and/or image processing in order to identify the reflection feature. The image analysis and/or image processing may use at least one feature detection algorithm. The image analysis and/or image processing may comprise one or more of the following: a filtering; a selection of at least one region of interest; a formation of a difference image between an image created by the sensor signals and at least one offset; an inversion of sensor signals by inverting an image created by the sensor signals; a formation of a difference image between an image created by the sensor signals at different times; a background correction; a decomposition into color channels; a decomposition into hue; saturation; and brightness channels; a frequency decomposition; a singular value decomposition; applying a blob detector; applying a corner detector; applying a Determinant of Hessian filter; applying a principle curvature-based region detector; applying a maximally stable extremal regions detector; applying a generalized Hough-transformation; applying a ridge detector; applying an affine invariant feature detector; applying an affine-adapted interest point operator; applying a Harris affine region detector; applying a Hessian affine region detector; applying a scale-invariant feature transform; applying a scale-space extrema detector; applying a local feature detector; applying speeded up robust features algorithm; applying a gradient location and orientation histogram algorithm; applying a histogram of oriented gradients descriptor; applying a Deriche edge detector; applying a differential edge detector; applying a spatio-temporal interest point detector; applying a Moravec corner detector; applying a Canny edge detector; applying a Laplacian of Gaussian filter; applying a Difference of Gaussian filter; applying a Sobel operator; applying a Laplace operator; applying a Scharr operator; applying a Prewitt operator; applying a Roberts operator; applying a Kirsch operator; applying a high-pass filter; applying a low-pass filter; applying a Fourier transformation; applying a Radon-transformation; applying a Hough-transformation; applying a wavelet-transformation; a thresholding; creating a binary image. Specifically, the evaluation of the image comprises selecting the region of interest in the image. The region of interest may be determined manually by a user or may be determined automatically, such as by recognizing an object within an image generated by the sensor element. For example, in case of a spot-like reflection feature the region of interest may be selected as a region around the spot profile.

For example, the illumination source 128 may be adapted to generate and/or to project a cloud of points such that a plurality of illuminated regions is generated on the distance detector 134 and/or the matrix of optical sensors 118, for example the CMOS detector. Additionally, disturbances may be present on the distance detector 134 and/or the matrix of optical sensors such as disturbances due to speckles and/or extraneous light and/or multiple reflections. The evaluation device 120 may be adapted to determine at least one region of interest, for example one or more pixels illuminated by the light beam which are used for determination of the longitudinal coordinate of the object. For example, the evaluation device 120 may be adapted to perform a filtering method, for example, a blob-analysis and/or an edge filter and/or object recognition method.

The evaluation device 120 may be configured for performing at least one image correction. The image correction may comprise at least one background subtraction. The evaluation device 120 may be adapted to remove influences from background light from the reflection beam profile, for example, by an imaging without further illumination.

The evaluation device 120 may be configured for determining the material information by evaluating the beam profile of the image of the object 112. The beam profile of the image, also denoted reflection beam profile, may be selected from the group consisting of a trapezoid beam profile; a triangle beam profile; a conical beam profile and a linear combination of Gaussian beam profiles.

The image may be a two-dimensional function, f(x,y), wherein brightness and/or color values are given for any x,y-position in the image. The position may be discretized corresponding to the recording pixels. The brightness and/or color may be discretized corresponding to a bitdepth of the optical sensors. The image filter may be at least one mathematical operation applied to the beam profile and/or to the at least one specific region of the beam profile. Specifically, the image filter $\Phi$ maps an image f, or a region of interest in the image, onto a real number, $\Phi(f(x,y))=\varphi$, wherein $\varphi$ denotes a feature, in particular a material feature in case of material dependent image filters. Images may be subject to noise and the same holds true for features. Therefore, features may be random variables. The features may be normally distributed. If features are not normally distributed, they may be transformed to be normally distributed such as by a Box-Cox-Transformation.

The evaluation device may be configured for determining at least one material feature $\varphi_m$ by applying at least one material dependent image filter $\Phi$ to the image. The material dependent image filter may be at least one filter selected from the group consisting of: a luminance filter; a spot shape filter; a squared norm gradient; a standard deviation; a smoothness filter such as a Gaussian filter or median filter; a grey-level-occurrence-based contrast filter; a grey-level-occurrence-based energy filter; a grey-level-occurrence-based homogeneity filter; a grey-level-occurrence-based dissimilarity filter; a Law's energy filter; a threshold area filter; or a linear combination thereof; or a further material dependent image filter $\Phi_{other}$ which correlates to one or more of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof by $|\rho_{\Phi_{other},\Phi_m}| \geq 0.40$ with $\Phi_m$ being one of the luminance filter, the spot shape filter, the squared norm gradient, the standard deviation, the smoothness filter, the grey-level-occurrence-based energy filter, the grey-level-occurrence-based homogeneity filter, the grey-level-occurrence-based dissimilarity filter, the Law's energy filter, or the threshold area filter, or a linear combination thereof. The further material dependent image filter $\Phi_{other}$ may correlate to one or more of the material dependent image filters $\Phi_m$ by $|\rho_{\Phi other,\Phi m}| \geq 0.60$, preferably by $|\rho_{\Phi other,\Phi m}| \geq 0.80$.

The material dependent image filter may be at least one arbitrary filter $\Phi$ that passes a hypothesis testing. As used herein, the term "passes a hypothesis testing" refers to the fact that a Null-hypothesis $H_0$ is rejected and an alternative hypothesis $H_1$ is accepted. The hypothesis testing may comprise testing the material dependency of the image filter by applying the image filter to a predefined data set. The data set may comprise a plurality of beam profile images. As used herein, the term "beam profile image" refers to a sum of $N_B$ Gaussian radial basis functions, $$f_k(x, y) = \left| \Sigma_{l=0}^{N_B-1} g_{lk}(x, y) \right|,$$

$$g_{lk}(x, y) = a_{lk} e^{-(\alpha(x-x_{lk}))^2} e^{-(\alpha(y-y_{lk}))^2}$$

wherein each of the $N_B$ Gaussian radial basis functions is defined by a center ($x_{lk}$, $y_{lk}$), a prefactor, $\alpha_{lk}$, and an exponential factor $\alpha = 1/\epsilon$. The exponential factor is identical for all Gaussian functions in all images. The center-positions, $x_{lk}$, $y_{lk}$, are identical for all images $f_k$: ($x_0$, $x_1$, ..., $x_{N_B-1}$),($y_0$, $y_1$, ..., $y_{N_B-1}$). Each of the beam profile images in the dataset may correspond to a material classifier and a distance. The material classifier may be a label such as 'Material A', 'Material B', etc. The beam profile images may be generated by using the above formula for $f_k(x, y)$ in combination with the following parameter table:

| Image Index | Material classifier, Material Index | Distance z | Parameters |
|---|---|---|---|
| k = 0 | Skin, m = 0 | 0.4 m | ($a_{00}$, $a_{10}$, ..., $a_{N_B-10}$) |
| k = 1 | Skin, m = 0 | 0.6 m | ($a_{01}$, $a_{11}$, ..., $a_{N_B-11}$) |
| k = 2 | Fabric, m = 1 | 0.6 m | ($a_{02}$, $a_{12}$, ..., $a_{N_B-12}$) |
| . | . | . | . |
| . | . | . | . |
| k = N | Material J, m = J − 1 | | ($a_{0N}$, $a_{1N}$, ..., $a_{N_B-1N}$) |

The values for x, y, are integers corresponding to pixels with $$\binom{x}{y}$$

$\in [0, 1, \ldots 31]^2$. The images may have a pixel size of 32×32. The dataset of beam profile images may be generated by using the above formula for $f_k$ in combination with a parameter set to obtain a continuous description of $f_k$. The values for each pixel in the 32×32-image may be obtained by inserting integer values from 0, ..., 31 for x, y, in $f_k(x, y)$. For example, for pixel (6,9), the value $f_k(6,9)$ may be computed.

Subsequently, for each image $f_k$, the feature value $\varphi_k$ corresponding to the filter $\Phi$ may be calculated, $\varphi(f_k(x,y), z_k) = \varphi_k$, wherein $z_k$ is a distance value corresponding to the image $f_k$ from the predefined data set. This yields a dataset with corresponding generated feature values $\varphi_k$. The hypothesis testing may use a Null-hypothesis that the filter does not distinguish between material classifier. The Null-Hypothesis may be given by $H_0$: $\mu_1 = \mu_2 = \ldots = \mu_J$, wherein $\mu_m$ is the expectation value of each material-group corresponding to the feature values $\varphi_k$. Index m denotes the material group. The hypothesis testing may use as alternative hypothesis that the filter does distinguish between at least two material classifiers. The alternative hypothesis may be given by $H_1$: $\exists m, m': \mu_m \neq \mu_{m'}$. As used herein, the term "not distinguish between material classifiers" refers to that the expectation values of the material classifiers are identical. As used herein, the term "distinguishes material classifiers" refers to that at least two expectation values of the material classifiers differ. As used herein "distinguishes at least two material classifiers" is used synonymous to "suitable material classifier". The hypothesis testing may comprise at least one analysis of variance (ANOVA) on the generated feature values. In particular, the hypothesis testing may comprise determining a mean-value of the feature values for each of the J materials, i.e. in total. J mean values, $$\bar{\varphi}_m = \frac{\Sigma_i \varphi_{i,m}}{N_m},$$

for $m \in [0, 1, \ldots, J-1]$, wherein $N_m$ gives the number of feature values for each of the J materials in the predefined data set. The hypothesis testing may comprise determining a mean-value of all N feature values $$\bar{\varphi} = \frac{\Sigma_m \Sigma_i \varphi_{i,m}}{N}.$$

The hypothesis testing may comprise determining a Mean Sum Squares within:

$$mssw = (\Sigma_m \Sigma_i (\varphi_{i,m} - \bar{\varphi})^2)(N-J).$$

The hypothesis testing may comprise determining a Mean Sum of Squares between, $$mssb = (\Sigma_m (\bar{\varphi}_m - \bar{\varphi})^2 N_m)/(J-1).$$

The hypothesis testing may comprise performing an F-Test:

$$CDF(x) = I_{\frac{d_1 x}{d_1 x + d_2}}\left(\frac{d_1}{2}, \frac{d_2}{2}\right),$$

where $d_1 = N-J$, $d_2 = J-1$,
$F(x) = 1 - CDF(x)$
$p = F(mssb/mssw)$

Herein, $I_x$ is the regularized incomplete Beta-Function, $$I_x(a, b) = \frac{B(x; a, b)}{B(a, b)},$$

with the Euler Beta-Function $B(a,b) = \int_0^1 t^{a-1}(1-t)^{b-1} dt$ and $B(x;a,b) = \int_0^x t^{a-1}(1-t)^{b-1} dt$ being the incomplete Beta-Function. The image filter may pass the hypothesis testing if a p-value, p, is smaller or equal than a pre-defined level of significance. The filter may pass the hypothesis testing if $p \leq 0.075$, preferably $p \leq 0.05$, more preferably $p \leq 0.025$, and most preferably $p \leq 0.01$. For example, in case the pre-defined level of significance is $\alpha = 0.075$, the image filter may pass the hypothesis testing if the p-value is smaller than $\alpha = 0.075$. In this case the Null-hypothesis $H_0$ can be rejected and the alternative hypothesis $H_1$ can be accepted. The image filter thus distinguishes at least two material classifiers. Thus, the image filter passes the hypothesis testing.

In the following, image filters are described assuming that the reflection image comprises at least one reflection feature, in particular a spot image. A spot image $f$ may be given by a function $f: \mathbb{R}^2 \to \mathbb{R}_{\geq 0}$, wherein the background of the image f may be already subtracted. However, other reflection features may be possible.

For example, the material dependent image filter may be a luminance filter. The luminance filter may return a luminance measure of a spot as material feature. The material feature may be determined by $$\varphi_m = \Phi(f, z) = -\int f(x) dx \frac{z^2}{d_{ray} \cdot n},$$

where f is the spot image. The distance of the spot is denoted by z, where z may be obtained for example by using a depth-from-defocus or depth-from-photon ratio technique and/or by using a triangulation technique. The surface normal of the material is given by $n \in \mathbb{R}^3$ and can be obtained as the normal of the surface spanned by at least three measured points. The vector $d_{ray} \in \mathbb{R}^3$ is the direction vector of the light source. Since the position of the spot is known by using a depth-from-defocus or depth-from-photon ratio technique and/or by using a triangulation technique wherein the position of the light source is known as a parameter of the detector system, $d_{ray}$, is the difference vector between spot and light source positions.

For example, the material dependent image filter may be a filter having an output dependent on a spot shape. This material dependent image filter may return a value which correlates to the translucence of a material as material feature. The translucence of materials influences the shape of the spots. The material feature may be given by $$\varphi_m = \Phi(f) = \frac{\int H(f(x) - \alpha h) dx}{\int H(f(x) - \beta h) dx},$$

wherein $0 < \alpha$, $\beta < 1$ are weights for the spot height h, and H denotes the Heavyside function, i.e. $H(x) = 1$: $x \geq 0$, $H(x) = 0$: $x < 0$. The spot height h may be determined by $$h = \int_{B_r} f(x) dx,$$

where $B_r$ is an inner circle of a spot with radius r.

For example, the material dependent image filter may be a squared norm gradient. This material dependent image filter may return a value which correlates to a measure of soft and hard transitions and/or roughness of a spot as material feature. The material feature may be defined by $$\varphi_m = \Phi(f) = \int \|\nabla f(x)\|^2 dx.$$

For example, the material dependent image filter may be a standard deviation. The standard deviation of the spot may be determined by $$\varphi_m = \Phi(f) = \int (f(x) - \mu)^2 dx,$$

Wherein $\mu$ is the mean value given by $\mu = \int (f(x)) dx$.

For example, the material dependent image filter may be a smoothness filter such as a Gaussian filter or median filter. In one embodiment of the smoothness filter, this image filter may refer to the observation that volume scattering exhibits less speckle contrast compared to diffuse scattering materials. This image filter may quantify the smoothness of the spot corresponding to speckle contrast as material feature. The material feature may be determined by $$\varphi_m = \Phi(f, z) = \frac{\int |\mathcal{F}(f)(x) - f(x)| dx}{\int f(x) dx} \cdot \frac{1}{z},$$

wherein $\mathcal{F}$ is a smoothness function, for example a median filter or Gaussian filter. This image filter may comprise dividing by the distance z, as described in the formula above. The distance z may be determined for example using a depth-from-defocus or depth-from-photon ratio technique and/or by using a triangulation technique. This may allow the filter to be insensitive to distance. In one embodiment of the smoothness filter, the smoothness filter may be based on the standard deviation of an extracted speckle noise pattern. A speckle noise pattern N can be described in an empirical way by $$f(x) = f_0(x) \cdot (N(X) + 1),$$

where $f_0$ is an image of a despeckled spot. N(X) is the noise term that models the speckle pattern. The computation of a despeckled image may be difficult. Thus, the despeckled image may be approximated with a smoothed version of f, i.e. $f_0 \approx \mathcal{F}(f)$, wherein $\mathcal{F}$ is a smoothness operator like a Gaussian filter or median filter. Thus, an approximation of the speckle pattern may be given by $$N(X) = \frac{f(x)}{\mathcal{F}(f(x))} - 1.$$

The material feature of this filter may be determined by $$\varphi_m = \Phi(f) = \sqrt{\operatorname{Var}\left(\frac{f}{\mathcal{F}(f)} - 1\right)},$$

Wherein Var denotes the variance function.

For example, the image filter may be a grey-level-occurrence-based contrast filter. This material filter may be based on the grey level occurrence matrix $M_{f,\rho}(g_1, g_2) = [p_{g_1, g_2}]$, whereas $p_{g_1, g_2}$ is the occurrence rate of the grey combination $(g_1, g_2) = [f(x_1, y_1), f(x_2, y_2)]$, and the relation $\rho$ defines the distance between $(x_1, y_1)$ and $(x_2, y_2)$, which is $\rho(x, y) = (x + a, y + b)$ with a and b selected from 0,1.

The material feature of the grey-level-occurrence-based contrast filter may be given by $$\varphi_m = \Phi(f) = \sum_{i,j=0}^{N-1} p_{ij}(i-j)^2.$$

For example, the image filter may be a grey-level-occurrence-based energy filter. This material filter is based on the grey level occurrence matrix defined above.

The material feature of the grey-level-occurrence-based energy filter may be given by $$\varphi_m = \Phi(f) = \sum_{i,j=0}^{N-1} (p_{ij})^2.$$

For example, the image filter may be a grey-level-occurrence-based homogeneity filter. This material filter is based on the grey level occurrence matrix defined above.

The material feature of the grey-level-occurrence-based homogeneity filter may be given by $$\varphi_m = \Phi(f) = \sum_{i,j=0}^{N-1} \frac{p_{ij}}{1+|i-j|}.$$

For example, the image filter may be a grey-level-occurrence-based dissimilarity filter. This material filter is based on the grey level occurrence matrix defined above.

The material feature of the grey-level-occurrence-based dissimilarity filter may be given by $$\varphi_m = \Phi(f) = -\sum_{i,j=0}^{N-1} \sqrt{p_{ij}\log(p_{ij})}.$$

For example, the image filter may be a Law's energy filter. This material filter may be based on the laws vector $L_5=[1, 4,6,4,1]$ and $E_5=[-1,-2,0,-2,-1]$ and the matrices $L_5(E_5)^T$ and $E_5(L_5)^T$.

The image $f_k$ is convoluted with these matrices:

$$f^*_{kL5E5}(x,y) = \sum_{i=-2}^{2}\sum_{j=-2}^{2} f_k(x+i,y+j)L_5(E_5)^T$$

and $$f^*_{kE5L5}(x,y) = \Sigma_{i=-2}^{2}\Sigma_{j=-2}^{2} f_k(x+i,y+j)E_5(L_5)^T.$$

$$E = \int \frac{f^*_{kL5E5}(x,y)}{\max(f^*_{kL5E5}(x,y))}dxdy,$$

$$F = \int \frac{f^*_{kE5L5}(x,y)}{\max(f^*_{kE5L5}(x,y))}dxdy,$$

Whereas the material feature of Law's energy filter may be determined by $$\varphi_m = \Phi(f) = E/F.$$

For example, the material dependent image filter may be a threshold area filter. This material feature may relate two areas in the image plane. A first area $\Omega_1$, may be an area wherein the function f is larger than $\alpha$ times the maximum of f. A second area $\Omega_2$, may be an area wherein the function f is smaller than $\alpha$ times the maximum of f, but larger than a threshold value $\varepsilon$ times the maximum of f. Preferably $\alpha$ may be 0.5 and $\varepsilon$ may be 0.05. Due to speckles or noise, the areas may not simply correspond to an inner and an outer circle around the spot center. As an example, $\Omega_1$ may comprise speckles or unconnected areas in the outer circle. The material feature may be determined by $$\varphi_m = \Phi(f) = \frac{\int_{\Omega_1} 1}{\int_{\Omega_2} 1},$$

wherein $\Omega_1=\{x|f(x)>\alpha\cdot\max(f(x))\}$ and $\Omega_2=\{x|\varepsilon\cdot\max(f(x))<f(x)<\alpha\cdot\max(f(x))\}$.

The material information m may be determined by using a predetermined relationship between $\varphi_m$ and m. The evaluation device may be configured for using at least one predetermined relationship between the material feature $\varphi_m$ and the material information of the object for determining the material information of the object. The predetermined relationship may be one or more of an empirical relationship, a semi-empiric relationship and an analytically derived relationship. The evaluation device may comprise at least one data storage device for storing the predetermined relationship, such as a lookup list or a lookup table.

In the ideal case, an image filter would yield features that are only dependent on material properties. However, image filters used in beam profile analysis may yield features that depend on distance and material properties, such as translucency. At least one of the material dependent image filter may be a function of the distance. The evaluation device may be configured for determining whether the used material dependent image filter is a function of the distance. Specifically, the evaluation device may be configured for determining a correlation coefficient of the material dependent image filter and the method used for determining the distance information. In case the correlation coefficient of the material dependent image filter with the method used for determining the distance information is close to 1 or −1, the distance may be projected out, by projecting the material feature on the principal axis with the lowest variance. As an example, the material feature may be projected onto an axis orthogonal to the correlating main component. In other words, the material feature may be projected onto the second main component. This may be done using a principal component analysis as known to the person skilled in the art.

The material information may be determined by evaluating $\varphi_m$ subsequently after determining of the longitudinal coordinate z such that the information about the longitudinal coordinate z can be considered for evaluating of $\varphi_m$. Specifically, the material information m may be determined by a function $m(z,\varphi_m)$. The function may be predefined and/or predetermined. For example, the function may be a linear function.

Subsequently, for each image $f_k$, the feature value $\varphi_k$ corresponding to the filter $\Phi$ may be calculated, $\Phi(f_k(x,y), z_k)=\varphi_k$, wherein $z_k$ is a distance value corresponding to the image $f_k$ from the predefined data set. This yields a dataset with corresponding generated feature values $\varphi_k$.

The hypothesis testing may use a Null-hypothesis that the filter does not distinguish between material classifier. The Null-Hypothesis may be given by $H_0: \mu_1=_2= \ldots =\mu_J$, wherein $\mu_m$ is the expectation value of each material-group corresponding to the feature values $\varphi_k$. Index m denotes the material group. The hypothesis testing may use as alternative hypothesis that the filter does distinguish between at least two material classifiers. The alternative hypothesis may be given by $H_1: \exists m, m': \mu_m \neq \mu_{m'}$. As used herein, the term "not distinguish between material classifiers" refers to that the expectation values of the material classifiers are identical. As used herein, the term "distinguishes material classifiers" refers to that at least two expectation values of the material classifiers differ. As used herein "distinguishes at least two material classifiers" is used synonymous to "suitable material classifier". The hypothesis testing may comprise at least one analysis of variance (ANOVA) on the generated feature values. In particular, the hypothesis testing may comprise determining a mean-value of the feature values for each of the J materials, i.e. in total J mean values, $$\overline{\varphi}_m = \frac{\sum_k \varphi_{i,m}}{N_m},$$

for $m \in [0, 1, \ldots, J-1]$, wherein $N_m$ gives the number of feature values for each of the J materials in the predefined data set. The hypothesis testing may comprise determining a mean-value of all N feature values $$\overline{\varphi} = \frac{\sum_m \sum_k \varphi_{i,m}}{N}.$$

The hypothesis testing may comprise determining a Mean Sum Squares within:

$$mssw = (\Sigma_m \Sigma_i (\varphi_{i,m} - \overline{\varphi})^2)/(N-J).$$

The hypothesis testing may comprise determining a Mean Sum of Squares between, $$mssb = (\Sigma_m (\overline{\varphi}_m - \overline{\varphi})^2 N_m)/(J-1).$$

The hypothesis testing may comprise performing an F-Test:

$$CDF(x) = I_{\frac{d_1 x}{d_1 x + d_2}}\left(\frac{d_1}{2}, \frac{d_2}{2}\right),$$

where $d_1 = N-J$, $d_2 = J-1$,
F(x) = 1 − CDF(x)
p = F(mssb/mssw)
Herein, $I_x$ is the regularized incomplete Beta-Function, $$I_x(a, b) = \frac{B(x; a, b)}{B(a, b)},$$

with the Euler Beta-Function $B(a,b) = \int_0^1 t^{a-1}(1-t)^{b-1} dt$ and $B(x;a,b) = \int_0^x t^{a-1}(1-t)^{b-1} dt$ being the incomplete Beta-Function. The image filter may pass the hypothesis testing if a p-value, p, is smaller or equal than a pre-defined level of significance. The filter may pass the hypothesis testing if $p \leq 0.075$, preferably $p \leq 0.05$, more preferably $p \leq 0.025$, and most preferably $p \leq 0.01$. For example, in case the pre-defined level of significance is $\alpha = 0.075$, the image filter may pass the hypothesis testing if the p-value is smaller than $\alpha = 0.075$. In this case the Null-hypothesis $H_0$ can be rejected and the alternative hypothesis $H_1$ can be accepted. The image filter thus distinguishes at least two material classifiers. Thus, the image filter passes the hypothesis testing.

In the following, image filters are described assuming that the reflection image comprises at least one reflection feature, in particular a spot image. A spot image $f$ may be given by a function $f: \mathbb{R}^2 \to \mathbb{R}_{\geq 0}$, wherein the background of the image f may be already subtracted. However, other reflection features may be possible.

For example, the material dependent image filter may be a luminance filter. The luminance filter may return a luminance measure of a spot as material feature. The material feature may be determined by $$\varphi_m = \Phi(f, z) = -\int f(x) dx \frac{z^2}{d_{ray} \cdot n},$$

where f is the spot image. The distance of the spot is denoted by z, where z may be obtained for example by using a depth-from-defocus or depth-from-photon ratio technique and/or by using a triangulation technique. The surface normal of the material is given by $n \in \mathbb{R}^3$ and can be obtained as the normal of the surface spanned by at least three measured points. The vector $d_{ray} \in \mathbb{R}^3$ is the direction vector of the light source. Since the position of the spot is known by using a depth-from-defocus or depth-from-photon ratio technique and/or by using a triangulation technique wherein the position of the light source is known as a parameter of the detector system, $d_{ray}$, is the difference vector between spot and light source positions.

For example, the material dependent image filter may be a filter having an output dependent on a spot shape. This material dependent image filter may return a value which correlates to the translucence of a material as material feature. The translucence of materials influences the shape of the spots. The material feature may be given by $$\varphi_m = \Phi(f) = \frac{\int H(f(x) - \alpha h) dx}{\int H(f(x) - \beta h) dx},$$

wherein $0 < \alpha, \beta < 1$ are weights for the spot height h, and H denotes the Heavyside function, i.e. $H(x) = 1: x \geq 0$, $H(x) = 0: x < 0$. The spot height h may be determined by $$h = \int_{B_r} f(x) dx,$$

where $B_r$ is an inner circle of a spot with radius r.

For example, the material dependent image filter may be a squared norm gradient. This material dependent image filter may return a value which correlates to a measure of soft and hard transitions and/or roughness of a spot as material feature. The material feature may be defined by $$\varphi_m = \Phi(f) = \int \|\nabla f(x)\|^2 dx.$$

For example, the material dependent image filter may be a standard deviation. The standard deviation of the spot may be determined by $$\varphi_m = \Phi(f) = \int (f(x) - \mu)^2 dx,$$

Wherein $\mu$ is the mean value given by $\mu = \int (f(x)) dx$.

For example, the material dependent image filter may be a smoothness filter such as a Gaussian filter or median filter. In one embodiment of the smoothness filter, this image filter may refer to the observation that volume scattering exhibits less speckle contrast compared to diffuse scattering materials. This image filter may quantify the smoothness of the spot corresponding to speckle contrast as material feature. The material feature may be determined by $$\varphi_m = \Phi(f, z) = \frac{\int |\mathcal{F}(f)(x) - f(x)| dx}{\int f(x) dx} \cdot \frac{1}{z},$$

wherein $\mathcal{F}$ is a smoothness function, for example a median filter or Gaussian filter. This image filter may comprise dividing by the distance z, as described in the formula above. The distance z may be determined for example using a depth-from-defocus or depth-from-photon ratio technique and/or by using a triangulation technique. This may allow the filter to be insensitive to distance. In one embodiment of the smoothness filter, the smoothness filter may be based on the standard deviation of an extracted speckle noise pattern. A speckle noise pattern N can be described in an empirical way by $$f(x)=f_0(x)\cdot(N(X)+1),$$

where $f_0$ is an image of a despeckled spot. N(X) is the noise term that models the speckle pattern. The computation of a despeckled image may be difficult. Thus, the despeckled image may be approximated with a smoothed version of f, i.e. $f_0 \approx \mathcal{F}(f)$, wherein $\mathcal{F}$ is a smoothness operator like a Gaussian filter or median filter. Thus, an approximation of the speckle pattern may be given by $$N(X) = \frac{f(x)}{\mathcal{F}(f(x))} - 1.$$

The material feature of this filter may be determined by $$\varphi_m = \Phi(f) = \sqrt{\mathrm{Var}\left(\frac{f}{\mathcal{F}(f)} - 1\right)},$$

Wherein Var denotes the variance function.

For example, the image filter may be a grey-level-occurrence-based contrast filter. This material filter may be based on the grey level occurrence matrix $M_{f,\rho}(g_1,g_2)=[p_{g1,g2}]$, whereas $p_{g1,g2}$ is the occurrence rate of the grey combination $(g_1,g_2)=[f(x_1,y_1),f(x_2,y_2)]$, and the relation $\rho$ defines the distance between $(x_1,y_1)$ and $(x_2,y_2)$, which is $\rho(x,y)=(x+a, y+b)$ with a and b selected from 0,1.

The material feature of the grey-level-occurrence-based contrast filter may be given by $$\varphi_m = \Phi(f) = \sum_{i,j=0}^{N-1} p_{ij}(i-j)^2.$$

For example, the image filter may be a grey-level-occurrence-based energy filter. This material filter is based on the grey level occurrence matrix defined above.

The material feature of the grey-level-occurrence-based energy filter may be given by $$\varphi_m = \Phi(f) = \sum_{i,j=0}^{N-1} (p_{ij})^2.$$

For example, the image filter may be a grey-level-occurrence-based homogeneity filter. This material filter is based on the grey level occurrence matrix defined above.

The material feature of the grey-level-occurrence-based homogeneity filter may be given by $$\varphi_m = \Phi(f) = \sum_{i,j=0}^{N-1} \frac{p_{ij}}{1+|i-j|}.$$

For example, the image filter may be a grey-level-occurrence-based dissimilarity filter. This material filter is based on the grey level occurrence matrix defined above.

The material feature of the grey-level-occurrence-based dissimilarity filter may be given by $$\varphi_m = \Phi(f) = -\sum_{i,j=0}^{N-1} \sqrt{p_{ij}\log(p_{ij})}.$$

For example, the image filter may be a Law's energy filter. This material filter may be based on the laws vector $L_5=[1, 4,6,4,1]$ and $E_5=[-1,-2,0,-2,-1]$ and the matrices $L_5(E_5)^T$ and $E_5(L_5)^T$.

The image $f_k$ is convoluted with these matrices:

$$f^*_{k,L5E5}(x,y) = \sum_{i=-2}^{2}\sum_{j=-2}^{2} f_k(x+i, y+j)L_5(E_5)^T$$

and $$f^*_{k,E5L5}(x,y) = \sum_{i=-2}^{2}\sum_{j=-2}^{2} f_k(x+i, y+j)E_5(L_5)^T.$$

$$E = \int \frac{f^*_{k,L5E5}(x,y)}{\max(f^*_{k,L5E5}(x,y))}dxdy,$$

$$F = \int \frac{f^*_{k,E5L5}(x,y)}{\max(f^*_{k,E5L5}(x,y))}dxdy,$$

Whereas the material feature of Law's energy filter may be determined by $$\varphi_m = \Phi(f) = E/F.$$

For example, the material dependent image filter may be a threshold area filter. This material feature may relate two areas in the image plane. A first area $\Omega 1$, may be an area wherein the function f is larger than $\alpha$ times the maximum of f. A second area $\Omega 2$, may be an area wherein the function f is smaller than $\alpha$ times the maximum of f, but larger than a threshold value $\varepsilon$ times the maximum of f. Preferably $\alpha$ may be 0.5 and $\varepsilon$ may be 0.05. Due to speckles or noise, the areas may not simply correspond to an inner and an outer circle around the spot center. As an example, $\Omega 1$ may comprise speckles or unconnected areas in the outer circle. The material feature may be determined by $$\varphi_m = \Phi(f) = \frac{\int_{\Omega 1} 1}{\int_{\Omega 2} 1},$$

wherein $\Omega 1=\{x|f(x)>\alpha\cdot\max(f(x))\}$ and $\Omega 2=\{x|\varepsilon\cdot\max(f(x))<f(x)<\alpha\cdot\max(f(x))\}$.

The material information m may be determined by using a predetermined relationship between $\varphi_m$ and m. The evaluation device 120 may be configured for using at least one predetermined relationship between the material feature $\varphi_m$ and the material information of the object for determining the material information of the object. The predetermined relationship may be one or more of an empirical relationship, a semi-empiric relationship and an analytically derived relationship. The evaluation device 120 may comprise at least one data storage device for storing the predetermined relationship, such as a lookup list or a lookup table.

In the ideal case, an image filter would yield features that are only dependent on material properties. However, image filters used in beam profile analysis may yield features that depend on distance and material properties, such as translucency. At least one of the material dependent image filter may be a function of the distance. The evaluation device 120 may be configured for determining whether the used material dependent image filter is a function of the distance. Specifically, the evaluation device 120 may be configured for determining a correlation coefficient of the material dependent image filter and the method used for determining the distance information. In case the correlation coefficient of the material dependent image filter with the method used for determining the distance information is close to 1 or −1, the distance may be projected out, by projecting the material feature on the principal axis with the lowest variance. As an example, the material feature may be projected onto an axis orthogonal to the correlating main component. In other words, the material feature may be projected onto the second main component. This may be done using a principal component analysis as known to the person skilled in the art.

The material information may be determined by evaluating $\varphi_m$ subsequently after determining of the longitudinal coordinate z such that the information about the longitudinal coordinate z can be considered for evaluating of $\varphi_m$. Specifically, the material information m may be determined by a function $m(z,\varphi_m)$. The function may be predefined and/or predetermined. For example, the function may be a linear function.

Additionally or alternatively, the evaluation device 120 may be configured for determining the material information by one or more of: comparative image analysis such as based on comparison of the image of the object 112 to an object library; material property analysis such as by comparison of parameters determined from the image of the object 112 to a database with stored parameters such as color, translucency, state of matter or the like. The evaluation device 120 may comprise at least one database, such as the database 140, comprising the object library and/or stored parameters such as a list and/or table of possible objects and possible parameters, such as a lookup list or a lookup table. The object library may comprise images of different objects to which the determined image of the object can be compared. The evaluation device 120 may be configured to determined via image analysis at least one parameter of the object such as reflectivity, color, translucency, state such as liquid or solid, roughness and the like.

The evaluation device 120 may be configured for performing at least one spectroscopic analysis of the determined intensities considering the determined distance information and the material information. The material information may be used for pre-classifying the object, specifically before performing the spectroscopic analysis, in particular before performing the spectroscopic measurement and/or the evaluation of the determined spectrum. The spectrometer device 110 may be configured for selecting at least one analyte of interest depending on the material information and may perform the spectroscopic measurement for the selected analyte of interest. Additionally or alternatively, the material information may be used as input parameter for the evaluation of the determined spectrum which may allow speeding up the evaluation.

The spectrometer device 110 may comprise at least one display device 142 configured for displaying the material information. The displaying of the material information may comprise arbitrary form of presentation such as graphically displaying the material information.

The display device 142 may, e.g. additionally, be configured for displaying a suggestion for the kind of material or product the object 112 may be. As an example, the material information may be "a white liquid" or "white translucent liquid" and the display device may display a list of suggestions such as paint, milk, cream, yoghurt, dough, starch, or the like.

The spectrometer device 110 may be configured for selecting at least one analyte of interest depending on the material information. For example, the evaluation device 120 may comprise a database in which material information and associated analytes of interests are stored. The display device 142 may provide the list of potential analytes of interest. The spectrometer device 110 may comprise at least one human-machine interface configured to permit a user to select at least one analyte of the list. The spectrometer device 110 may be configured to perform at least one spectroscopic analysis for the selected analyte of interest. Thus, it may be possible to allow providing material information of the sample, specifically, before determining the spectroscopic information, in order to facilitate the application for the user. As an example, the spectrometer device 110 may allow detecting whether a sample is milk, in order to display the fat or lactose content.

LIST OF REFERENCE NUMBERS 110 spectrometer device
112 object
114 wavelength selective element
116 pixelated optical detector
118 optical sensor
120 evaluation device
121 Imaging detector
122 interface
124 transfer device
126 light beam
128 illumination source
130 housing
132 optical axis
134 distance detector
136 illumination light beam
138 divider
140 database
142 display device

The invention claimed is:

1. A spectrometer device configured for determining at least one spectral or spectroscopic information of at least one object,
    wherein the spectrometer device is configured for determining intensities of constituent wavelength signals of at least one light beam propagating from the at least one object to the spectrometer device, wherein the spectrometer device comprises at least one distance detector,
    wherein the at least one distance detector is configured for determining at least one distance information about a distance between the at least one object and the spectrometer device, wherein the spectrometer device comprises at least one pixelated imaging detector configured for determining at least one image of the at least one object,
    wherein the spectrometer device comprises at least one evaluation device, wherein the at least one evaluation device is configured for determining at least one material information of the at least one object by evaluating at least one image of the at least one object determined by the at least one pixelated imaging detector,
    wherein the at least one evaluation device is configured for determining the material information by applying at least one material dependent image filter Φ to the image of the at least one object determined by the at least one pixelated imaging detector, wherein the at least one material dependent image filter is an image filter having a material dependent output, wherein the at least one material dependent image filter comprises a luminance filter; wherein the luminance filter returns a luminance measure of a spot as material feature, wherein the material feature Φm is determined by $$\varphi_m = \Phi(f, z) = -\int f(x)dx \frac{z^2}{d_{ray} \cdot n},$$

where f is a spot image, x denote the pixels of the imaging detector, n is a surface normal of the material, z is the distance, wherein a position of a light source is known as a parameter of the spectrometer device and $dr_{ay}$ is a difference vector between spot and light source positions, wherein the at least one evaluation device is configured for performing at least one spectroscopic analysis of the determined intensities of constituent wavelength signals considering the determined distance information and the material information, wherein the at least one evaluation device is configured for using the material information for pre-classifying the at least one object before performing a spectroscopic measurement and/or an evaluation of a determined spectrum.

2. The spectrometer device according to claim 1, wherein the spectrometer device is a mobile spectrometer device.

3. The spectrometer device according to claim 1, wherein the spectrometer device further comprises at least one wavelength selective element configured for separating incident light into a spectrum of constituent wavelength signals, wherein respective intensities of the constituent wavelength signals are determined by employing at least one pixelated optical detector comprising a plurality of pixels, and/or at least one single pixel optical detector.

4. The spectrometer device according to claim 1, wherein the at least one spectroscopic analysis comprises determining at least one difference in at least one light property due to presence of the at least one object, wherein the difference in the light property is selected from the group consisting of: at least one wavelength dependent intensity difference; and at least one wavelength dependent polarization difference.

5. The spectrometer device according to claim 4, wherein the at least one distance information is obtained by using one or more of the techniques selected from the group consisting of: depth-from-photon-ratio, structured light, beam profile analysis, time-of-flight, shape-from-motion, depth-from-focus, triangulation, depth-from-defocus, and stereo sensors.

6. The spectrometer device according to claim 1, wherein the at least one distance detector comprises at least one sensor element having a matrix of optical sensors, the optical sensors each having a light-sensitive area, wherein each optical sensor is configured for generating at least one sensor signal in response to an illumination of the light-sensitive area by at least one light beam propagating from the at least one object to the spectrometer device, wherein at least one first optical sensor of the optical sensors is adapted to generate a first sensor signal in response to illumination by a first constituent wavelength and wherein at least one second optical sensor of the optical sensors is adapted to generate a second sensor signal in response to an illumination by the first constituent wavelength, wherein the at least one evaluation device is configured for determining at least one longitudinal coordinate z of the at least one object by evaluating a combined signal Q from the first sensor signal and the second sensor signal.

7. The spectrometer device according to claim 6, wherein the combined signal Q is derived by one or more of: forming a quotient of the first signal and the second signal or vice versa; forming a quotient of a multiple of the first signal and a multiple of the second signal or vice versa; forming a quotient of a linear combination of the first signal and a linear combination of the second signal or vice versa; or forming a quotient of a first linear combination of the first signal and the second signal and a second linear combination of the first signal and the second signal, wherein the at least one evaluation device is configured for using at least one predetermined relationship between the combined signal Q and the longitudinal coordinate z of the at least one object for determining the longitudinal coordinate z.

8. The spectrometer device according to claim 1, wherein the at least one material information is at least one property selected from the group consisting of: a scattering coefficient, a translucency, a transparency, a deviation from a Lambertian surface reflection, a speckle, material and/or material class; and object type and/or object class.

9. The spectrometer device according to claim 1, wherein the at least one material dependent image filter is at least one filter that passes a hypothesis testing, wherein the hypothesis testing uses a Null-hypothesis that the at least one filter does not distinguish between material classifiers and an alternative hypothesis that the at least one filter distinguishes at least two material classifiers, wherein the at least one filter passes the hypothesis testing if a p-value, p, is smaller or equal than a pre-defined level of significance, wherein $p \leq 0.075$.

10. The spectrometer device according to claim 9, wherein $p \leq 0.05$.

11. The spectrometer device according to claim 9, wherein $p \leq 0.025$.

12. The spectrometer device according to claim 9, wherein $p \leq 0.01$.

13. The spectrometer device according to claim 1, wherein the at least one evaluation device is configured for determining the material information by one or more of: comparative image analysis based on comparison of the image of the at least one object to an object library; or material property analysis by comparison of parameters determined from the image of the at least one object to a database with stored parameters selected from the group consisting of color, translucency, and state of matter.

14. The spectrometer device according to claim 1, wherein the spectrometer device comprises at least one display device configured for displaying the material information.

15. The spectrometer device according to claim 1, wherein the spectrometer device is configured for selecting at least one analyte of interest depending on the material information, wherein the spectrometer device is configured to perform at least one spectroscopic analysis for the selected analyte of interest.

16. The spectrometer device according to claim 1, wherein the at least one pixelated imaging detector is at least one detector selected from the group consisting of: at least one CCD detector; at least one CMOS detector; and at least one InGaAs detector.

17. A method for determining at least one difference in at least one light property of at least one light beam originating from at least one object, wherein in the method a spectrometer device according to claim 1 is used, the method comprising the following steps:
- determining intensities of constituent wavelength signals of at least one light beam propagating from the at least one object to the spectrometer device;
- determining at least one distance information about a distance z between the at least one object and the spectrometer device by using at least one distance detector;
- determining at least one material information of the at least one object by evaluating of at least one image of the at least one object determined by at least one pixelated imaging detector of the spectrometer device by using at least one evaluation device,
- wherein the material information is determined by applying at least one material dependent image filter $\Phi$ to the image of the at least one object determined by the at least one pixelated imaging detector, wherein the material dependent image filter is an image filter having a material dependent output,
- wherein the at least one material dependent image filter comprises a luminance filter; wherein the luminance filter returns a luminance measure of a spot as material feature, wherein the material feature $\emptyset m$ is determined by $$\varphi_m = \Phi(f, z) = -\int f(x) dx \frac{z^2}{d_{ray} \cdot n},$$

where f is a spot image, x denote the pixels of the imaging detector, n is a surface normal of the material, z is the distance, wherein a position of a light source is known as a parameter of the spectrometer device and $dr_{ay}$ is a difference vector between spot and light source positions, and performing at least one spectroscopic analysis of the determined intensities of constituent wavelength signals considering the determined distance information and the material information, wherein the at least one evaluation device is configured for using the material information for pre-classifying the at least one object before performing a spectroscopic measurement and/or an evaluation of a determined spectrum.

18. A method of using the spectrometer device according to claim 1, the method comprising using the spectrometer device for an application selected from the group consisting of: an infrared detection application; a spectroscopy application; an exhaust gas monitoring application; a combustion process monitoring application; a pollution monitoring application; an industrial process monitoring application; a chemical process monitoring application; a food processing process monitoring application; a water quality monitoring application; an air quality monitoring application; a quality control application; a temperature control application; a motion control application; an exhaust control application; a gas sensing application; a gas analytics application; a motion sensing application; a chemical sensing application; a mobile application; a medical application; a mobile spectroscopy application; a food analysis application; an agricultural application; characterization of soil, silage, feed, crop or produce, monitoring plant health; and a plastics identification and/or recycling application.

\* \* \* \* \*